United States Patent [19]

Munroe et al.

[11] Patent Number: 6,077,949
[45] Date of Patent: Jun. 20, 2000

[54] CLONED GLUCAGON-LIKE PEPTIDE 2 RECEPTORS

[75] Inventors: Donald G. Munroe, Waterdown; Ashwani K. Gupta, Mississauga; Tejal B. Vyas, Mississauga; Kirk McCallum, Mississauga; Ermei Fan, Toronto, all of Canada

[73] Assignee: Allelix Biopharmaceuticals, Inc., Ontario, Canada

[21] Appl. No.: 08/845,546

[22] Filed: Apr. 24, 1997

Related U.S. Application Data

[63] Continuation-in-part of application No. 08/767,224, Dec. 13, 1996, abandoned.
[51] Int. Cl.[7] .............................. C12N 15/12; C07K 14/72
[52] U.S. Cl. ........................ 536/23.5; 435/69.1; 435/325; 435/252.3; 435/320.1
[58] Field of Search ................................ 536/23.5, 24.31; 435/325, 320.1, 69.1, 252.3

[56] References Cited

U.S. PATENT DOCUMENTS

| 5,494,806 | 2/1996 | Segre et al. ............................ 435/69.1 |
| 5,776,725 | 7/1998 | Kindsvogel et al. .................. 435/69.1 |

OTHER PUBLICATIONS

MacNeil, et al. (1994) *Biochem. Biophys. Res. Comm.* 198: 328–34.

Ishihara, et al. (1991) *EMBO J.* 10: 1635–41.

*Primary Examiner*—David L. Fitzgerald
*Attorney, Agent, or Firm*—Pennie & Edmonds LLP

[57] ABSTRACT

The invention relates to nucleotides and amino acid sequences encoding glucagon-like peptide 2 receptors, recombinant host cells transformed with such nucleotides, and methods of using the same in drug screening and related applications.

9 Claims, 11 Drawing Sheets

```
   1  TCTCCACTCC CAACAGATGC GTCTGCTGTG GGGCCCTGGG AGGCCCTTCC
  51  TCGCCCTGCT TCTGCTGGTT TCCATCAAGC AAGTTACAGG ATCGCTCCTC
 101  AAGGAGACAA CTCAGAAGTG GGCTAATTAT AAGGAGAAGT GTCTGGAAGA
 151  CTTGCACAAT AGACTTTCTG GCATATTTTG TAATGGGACA TTTGATCGGT
 201  ATGTGTGCTG GCCTCATTCT TATCCTGGAA ATGTCTCTGT TCCCTGTCCT
 251  TCATACTTAC CTTGGTGGAA TGCAGAGAGC CCAGGAAGGG CCTACAGACA
 301  CTGCTTGGCT CAGGGGACTT GGCAGACGCG AGAGAACACC ACAGATATTT
 351  GGCAGGATGA ATCAGAATGC TCAGAGAACC ACAGCTTCAG ACAAAACGTG
 401  GATCACTACG CCTTGCTATA CACCTTGCAG CTGATGTACA CTGTGGGCTA
 451  CTCCGTGTCT CTCATCTCCC TCTTCTTGGC TCTTACACTC TTCTTGTTCC
 501  TTCGAAAACT GCATTGCACA CGCAATTACA TCCACATGAA CCTGTTCGCT
 551  TCGTTCATCC TGAAAGTTCT GGCTGTCCTG GTGAAGGACA TGGTCTCCCA
 601  CAACTCTTAC TCCAAGAGGC CCGATGATGA GAGTGGATGG ATGTCATATC
 651  TGTCAGAGAC ATCCGTCTCC TGTCGCTCCG TCCAGGTCCT CCTGCACTAC
 701  TTTGTGGGCA CCAATCACTT GTGGCTGCTG GTTGAAGGAC TTTACCTCCA
 751  CACTCTGCTG GAGCCCACAG TGTTTCCTGA AAGGCGGCTG TGGCCCAAGT
 801  ACCTGGTGGT GGGTTGGGCC TTCCCCATGC TGTTTGTTAT TCCCTGGGGT
 851  TTTGCCCGTG CACACCTGGA GAACACACGG TGCTGGGCCA CAAATGGGAA
 901  CCTGAAAATC TGGTGGATCA TCAGAGGACC CATGCTGCTT TGTGTAACAG
 951  TTAATTTCTT CATCTTCCTC AAGATTCTCA AGCTTCTCAT TTCTAAGCTC
1001  AAAGCTCATC AGATGTGCTT CAGAGACTAC AAATACAGAT TGGCGAAATC
1051  AACGTTGCTC CTCATTCCTT TGTTGGGGGT TCATGAGGTC CTCTTCACTT
1101  TCTTCCCCGA CGACCAAGTT CAAGGATTTT CAAAACGTAT TCGACTCTTC
1151  ATCCAGCTGA CACTGAGCTC TGTCCACGGA TTTCTGGTGG CCTTGCAGTA
```

FIG.1A

1201 TGGCTTTGCC AATGGAGAGG TGAAGGCAGA GCTGCGAAAG TCATGGGGCC

1251 GCTTCTTATT AGCCCGCCAC TGGGGCTGCA GAACCTGTGT CCTGGGGAAG

1301 AATTTCCGGT TCCTGGGGAA GTGTTCCAAG AAGCTGTCGG AGGGAGATGG

1351 CTCTGAGACA CTCCAGAAGC TGCGGTTCTC CACATGCAGC TCACACCTGG

1401 CCTCTGAGAC CCTGGGAGAC GTTGGGGTAC AGCCTCACAG GGGCCGTGGA

1451 GCTTGGCCCC GGGGAAGCAG CCTGTCTGAG AGCAGTGAGG GAGACTTCAC

1501 CCTGGCCAAT ACGATGGAGG AGATTCTGGA AGAGAGTGAG ATCTAAGGCA

1551 GGGTCCATCA CCGCAGCTTG GCCA

FIG.1B

```
  1  MRLLWGPGRP  FLALLLLVSI  KQVTGSLLKE  TTQKWANYKE  KCLEDLHNRL

51  SGIFCNGTFD  RYVCWPHSYP  GNVSVPCPSY  LPWWNAESPG  RAYRHCLAQG
                                                           TM-1
101  TWQTRENTTD  IWQDESECSE  NHSFRQNVDH  YALLYTLQLM  YTVGYSVSLI
                   TM-2
151  SLFLALTLFL  FLRKLHCTRN  YIHMNLFASF  ILKVLAVLVK  DMVSHNSYSK
                                     TM-3
201  RPDDESGWMS  YLSETSVSCR  SVQVLLHYFV  GTNHLWLLVE  GLYLHTLLEP
                       TM-4
251  TVFPERRLWP  KYLVVGWAFP  MLFVIPWGFA  RAHLENTRCW  ATNGNLKIWW
              TM-5                                        TM-6
301  IIRGPMLLCV  TVNFFIFLKI  LKLLISKLKA  HQMCFRDYKY  RLAKSTLLLI
                                                         TM-7
351  PLLGVHEVLF  TFFPDDQVQG  FSKRIRLFIQ  LTLSSVHGFL  VALQYGFANG

401  EVKAELRKSW  GRFLLARHWG  CRTCVLGKNF  RFLGKCSKKL  SEGDGSETLQ

451  KLRFSTCSSH  LASETLGDVG  VQPHRGRGAW  PRGSSLSESS  EGDFTLANTM

501  EEILEESEI*
```

FIG.2

```
  1 TCCTTCTCTC TTATCTCCCT CTTCCTGGCT CTCACCCTCC TCTTGTTTCT
 51 TCGAAAACTC CACTGCACGC GCAACTACAT CCACATGAAC TTGTTTGCTT
101 CTTTCATCCT GAGAACCCTG GCTGTACTGG TGAAGGACGT CGTCTTCTAC
151 AACTCTTACT CCAAGAGGCC TGACAATGAG AATGGGTGGA TGTCCTACCT
201 GTCAGAGATG TCCACCTCCT GCCGCTCAGT CCAGGTTCTC TTGCATTACT
251 TTGTGGGTGC CAATTACTTA TGGCTGCTGG TTGAAGGCCT CTACCTCCAC
301 ACGCTGCTGG AGCCCACAGT GCTTCCTGAG AGGCGGCTGT GGCCCARATA
351 CCTGCTGTTG GGTTGGGCCT TCCCTGTGCT ATTTGTTGTA CCCTGGGGTT
401 TCGCCCGTGC ACACCTGGAG AACACAGGGT GCTGGACAAC AAATGGGAAT
451 AAGAAAATCT GGTGGATCAT CCGAGGACCC ATGATGCTCT GTGTAACAGT
501 CAATTTCTTC ATCTTCCTGA AAATTCTCAA GCTTCTCATT TCTAAGCTCA
551 AAGCTCATCA AATGTGCTTC AGAGATTATA AATACAGATT GGCAAAATCA
601 ACACTGGTCC TCATTCCTTT ATTGGGCGTT CATGAGATCC TCTTCTCTTT
651 CATCACTGAT GATCAAG
```

FIG.4

```
          S  F  S  L  I  S  L  F  L  A  L  T  L  L  L  F  L  R  K  L
       TCCTTCTCTCTTATCTCCCTCTTCCTGGCTCTCACCCTCCTCTTGTTTCTTCGAAAACTC
     1 ---------+---------+---------+---------+---------+---------+  60

H  C  T  R  N  Y  I  H  M  N  L  F  A  S  F  I  L  R  T  L
       CACTGCACGCGCAACTACATCCACATGAACTTGTTTGCTTCTTTCATCCTGAGAACCCTG
    61 ---------+---------+---------+---------+---------+---------+ 120

A  V  L  V  K  D  V  V  F  Y  N  S  Y  S  K  R  P  D  N  E
       GCTGTACTGGTGAAGGACGTCGTCTTCTACAACTCTTACTCCAAGAGGCCTGACAATGAG
   121 ---------+---------+---------+---------+---------+---------+ 180

N  G  W  M  S  Y  L  S  E  M  S  T  S  C  R  S  V  Q  V  L
       AATGGGTGGATGTCCTACCTGTCAGAGATGTCCACCTCCTGCCGCTCAGTCCAGGTTCTC
   181 ---------+---------+---------+---------+---------+---------+ 240

L  H  Y  F  V  G  A  N  Y  L  W  L  L  V  E  G  L  Y  L  H
       TTGCATTACTTTGTGGGTGCCAATTACTTATGGCTGCTGGTTGAAGGCCTCTACCTCCAC
   241 ---------+---------+---------+---------+---------+---------+ 300

T  L  L  E  P  T  V  L  P  E  R  R  L  W  P  X  Y  L  L  L
       ACGCTGCTGGAGCCCACAGTGCTTCCTGAGAGGCGGCTGTGGCCCARATACCTGCTGTTG
   301 ---------+---------+---------+---------+---------+---------+ 360

G  W  A  F  P  V  L  F  V  V  P  W  G  F  A  R  A  H  L  E
       GGTTGGGCCTTCCCTGTGCTATTTGTTGTACCCTGGGGTTTCGCCCGTGCACACCTGGAR
   361 ---------+---------+---------+---------+---------+---------+ 420

N  T  G  C  W  T  T  N  G  N  K  K  I  W  W  I  I  R  G  P
       AACACAGGGTGCTGGACAACAAATGGGAATAAGAAAATCTGGTGGATCATCCGAGGACCC
   421 ---------+---------+---------+---------+---------+---------+ 480

M  M  L  C  V  T  V  N  F  F  I  F  L  K  I  L  K  L  L  I
       ATGATGCTCTGTGTAACAGTCAATTTCTTCATCTTCCTGAAAATTCTCAAGCTTCTCATT
   481 ---------+---------+---------+---------+---------+---------+ 540

S  K  L  K  A  H  Q  M  C  F  R  D  Y  K  Y  R  L  A  K  S
       TCTAAGCTCAAAGCTCATCAAATGTGCTTCAGAGATTATAAATACAGATTGGCAAAATCA
   541 ---------+---------+---------+---------+---------+---------+ 600

T  L  V  L  I  P  L  L  G  V  H  E  I  L  F  S  F  I  T  D
       ACACTGGTCCTCATTCCTTTATTGGGCGTTCATGAGATCCTCTTCTCTTTCATCACTGAT
   601 ---------+---------+---------+---------+---------+---------+ 660

D  Q
       GATCAAG
   661 -------                                                      667
```

FIG.5

```
    TGGAGAGGATTTGTGCAAACATTTCTTCTGTGGACCAAGAGGAATGCAAGAGGAGGCTGC
1   ---------+---------+---------+---------+---------+---------+   60

CTGCCGTGCATCTTGGACGGCTAGAGAGATGTACCCCTACTTGTGAAGGTGCACGAGGAA
61  ---------+---------+---------+---------+---------+---------+   120

M  K  L  G  S  S  R  A  G  P  G  R  G  S  A  G  L  L  P  G
    GATGAAGCTGGGATCGAGCAGGGCAGGGCCTGGGAGAGGAAGCGCGGGACTCCTGCCTGG
121 ---------+---------+---------+---------+---------+---------+   180

V  H  E  L  P  M  G  I  P  A  P  W  G  T  S  P  L  S  F  H
    CGTCCACGAGCTGCCCATGGGCATCCCTGCCCCCTGGGGGACCAGTCCTCTCTCCTTCCA
181 ---------+---------+---------+---------+---------+---------+   240

R  K  C  S  L  W  A  P  G  R  P  F  L  T  L  V  L  L  V  S
    CAGGAAGTGCTCTCTCTGGGCCCCTGGGAGGCCCTTCCTCACTCTGGTCCTGCTGGTTTC
241 ---------+---------+---------+---------+---------+---------+   300

I  K  Q  V  T  G  S  L  L  E  E  T  T  R  K  W  A  Q  Y  K
    CATCAAGCAAGTTACAGGATCCCTCCTTGAGGAAACGACTCGGAAGTGGGCTCAGTACAA
301 ---------+---------+---------+---------+---------+---------+   360

Q  A  C  L  R  D  L  L  K  E  P  S  G  I  F  C  N  G  T  F
    ACAGGCATGTCTGAGAGACTTACTCAAGGAACCTTCTGGCATATTTTGTAACGGGACATT
361 ---------+---------+---------+---------+---------+---------+   420

D  Q  Y  V  C  W  P  H  S  S  P  G  N  V  S  V  P  C  P  S
    TGATCAGTACGTGTGTTGGCCTCATTCTTCTCCTGGAAATGTCTCTGTACCCTGCCCTTC
421 ---------+---------+---------+---------+---------+---------+   480

Y  L  P  W  W  S  E  E  S  S  G  R  A  Y  R  H  C  L  A  Q
    ATACTTACCTTGGTGGAGTGAAGAGAGCTCAGGAAGGGCCTACAGACACTGCTTGGCTCA
481 ---------+---------+---------+---------+---------+---------+   540

G  T  W  Q  T  I  E  N  A  T  D  I  W  Q  D  D  S  E  C  S
    GGGGACTTGGCAGACGATAGAGAACGCCACGGATATTTGGCAGGATGACTCCGAATGCTC
541 ---------+---------+---------+---------+---------+---------+   600

E  N  H  S  F  K  Q  N  V  D  R  Y  A  L  L  S  T  L  Q  L
    CGAGAACCACAGCTTCAAGCAAAACGTGGACCGTTATGCCTTGCTGTCAACCTTGCAGCT
601 ---------+---------+---------+---------+---------+---------+   660

M  Y  T  V  G  Y  S  F  S  L  I  S  L  F  L  A  L  T  L  L
    GATGTACACCGTGGGATACTCCTTCTCTCTTATCTCCCTCTTCCTGGCTCTCACCCTCCT
661 ---------+---------+---------+---------+---------+---------+   720
```

FIG.6A

```
              L  F  L  R  K  L  H  C  T  R  N  Y  I  H  M  N  L  F  A  S
           CTTGTTTCTTCGAAAACTCCACTGCACGCGCAACTACATCCACATGAACTTGTTTGCTTC
     721   ---------+---------+---------+---------+---------+---------+   780

F  I  L  R  T  L  A  V  L  V  K  D  V  V  F  Y  N  S  Y  S
           TTTCATCCTGAGAACCCTGGCTGTACTGGTGAAGGACGTCGTCTTCTACAACTCTTACTC
     781   ---------+---------+---------+---------+---------+---------+   840

K  R  P  D  N  E  N  G  W  M  S  Y  L  S  E  M  S  T  S  C
           CAAGAGGCCTGACAATGAGAATGGGTGGATGTCCTACCTGTCAGAGATGTCCACCTCCTG
     841   ---------+---------+---------+---------+---------+---------+   900

R  S  V  Q  V  L  L  H  Y  F  V  G  A  N  Y  L  W  L  L  V
           CCGCTCAGTCCAGGTTCTCTTGCATTACTTTGTGGGTGCCAATTACTTATGGCTGCTGGT
     901   ---------+---------+---------+---------+---------+---------+   960

E  G  L  Y  L  H  T  L  L  E  P  T  V  L  P  E  R  R  L  W
           TGAAGGCCTCTACCTCCACACGCTGCTGGAGCCCACAGTGCTTCCTGAGAGGCGGCTGTG
     961   ---------+---------+---------+---------+---------+---------+  1020

P  R  Y  L  L  G  W  A  F  P  V  L  F  V  V  P  W  G  F
           GCCCAGATACCTGCTGTTGGGTTGGGCCTTCCCTGTGCTATTTGTTGTACCCTGGGGTTT
    1021   ---------+---------+---------+---------+---------+---------+  1080

A  R  A  H  L  E  N  T  G  C  W  T  T  N  G  N  K  K  I  W
           CGCCCGTGCACACCTGGAGAACACAGGGTGCTGGACAACAAATGGGAATAAGAAAATCTG
    1081   ---------+---------+---------+---------+---------+---------+  1140

W  I  I  R  G  P  M  M  L  C  V  T  V  N  F  F  I  F  L  K
           GTGGATCATCCGAGGACCCATGATGCTCTGTGTAACAGTCAATTTCTTCATCTTCCTGAA
    1141   ---------+---------+---------+---------+---------+---------+  1200

I  L  K  L  L  I  S  K  L  K  A  H  Q  M  C  F  R  D  Y  K
           AATTCTCAAGCTTCTCATTTCTAAGCTCAAAGCTCATCAAATGTGCTTCAGAGATTATAA
    1201   ---------+---------+---------+---------+---------+---------+  1260

Y  R  L  A  K  S  T  L  V  L  I  P  L  L  G  V  H  E  I  L
           ATACAGATTGGCAAAATCAACACTGGTCCTCATTCCTTTATTGGGCGTTCATGAGATCCT
    1261   ---------+---------+---------+---------+---------+---------+  1320

F  S  F  I  T  D  D  Q  V  E  G  F  A  K  L  I  R  L  F  I
           CTTCTCTTTCATCACTGATGATCAAGTTGAAGGATTTGCAAAACTTATACGACTTTTCAT
    1321   ---------+---------+---------+---------+---------+---------+  1380
```

FIG. 6B

```
            Q  L  T  L  S  S  F  H  G  F  L  V  A  L  Q  Y  G  F  A  N
         TCAGTTGACACTGAGCTCCTTTCATGGGTTCCTGGTGGCCTTGCAGTATGGTTTTGCCAA
   1381  ---------+---------+---------+---------+---------+---------+  1440

G  E  V  K  A  E  L  R  K  Y  W  V  R  F  L  L  A  R  H  S
         TGGAGAAGTGAAGGCTGAGCTGCGGAAATACTGGGTCCGCTTCTTGCTAGCCCGCCACTC
   1441  ---------+---------+---------+---------+---------+---------+  1500

G  C  R  A  C  V  L  G  K  D  F  R  F  L  G  K  C  P  K  K
         AGGCTGCAGAGCCTGTGTCCTGGGGAAGGACTTCCGGTTCCTAGGAAAATGTCCCAAGAA
   1501  ---------+---------+---------+---------+---------+---------+  1560

L  S  E  G  D  G  A  E  K  L  R  K  L  Q  P  S  L  N  S  G
         GCTCTCGGAAGGAGATGGCGCTGAGAAGCTTCGGAAGCTGCAGCCCTCACTTAACAGTGG
   1561  ---------+---------+---------+---------+---------+---------+  1620

R  L  L  H  L  A  M  R  G  L  G  E  L  G  A  Q  P  Q  Q  D
         GCGGCTCCTACATCTAGCCATGCGAGGTCTTGGGGAGCTGGGCGCCCAGCCCCAACAGGA
   1621  ---------+---------+---------+---------+---------+---------+  1680

H  A  R  W  P  R  G  S  S  L  S  E  C  S  E  G  D  V  T  M
         CCATGCACGCTGGCCCCGGGGCAGCAGCCTGTCCGAGTGCAGTGAGGGGGATGTCACCAT
   1681  ---------+---------+---------+---------+---------+---------+  1740

A  N  T  M  E  E  I  L  E  E  S  E  I  *
         GGCCAACACCATGGAGGAGATTCTGGAAGAGAGTGAGATCTAGGGTGGAGTTCCACCACC
   1741  ---------+---------+---------+---------+---------+---------+  1800

CTGGCTCTGCTCCCAGGGACTCTTGAGGGGGCCCAGGAAGAGGAAGCAAAGCAGGACACA
   1801  ---------+---------+---------+---------+---------+---------+  1860

CGTTGCTGGGCACGGAATCATTCTCGTTCCATTCACCATGCCACTTTGATATGAAAGCTA
   1861  ---------+---------+---------+---------+---------+---------+  1920

TCACAAGGTTCTTCAAGCTCTGTATGAAAGAGGCTGTGTGTCATGCTCACAGCCTCTGCC
   1921  ---------+---------+---------+---------+---------+---------+  1980

TGCTCTTCTCATCCTAATAACCCCCACCAGTGTGTTTTCCACAATGCCCACCAGACCCTA
   1981  ---------+---------+---------+---------+---------+---------+  2040

GGGCCTGGCTCTAAATTCAAGCCAATGAAGTCCCACCCGGAATTCTTTTGCTTTTTACCC
   2041  ---------+---------+---------+---------+---------+---------+  2100

CTGGAAGAAATA
   2101  ---------+--  2112
```

FIG. 6C

```
  1  MKLGSSRAGP GRGSAGLLPG VHELPMGIPA PWGTSPLSFH RKCSLWAPGR
 51  PFLTLVLLVS IKQVTGSLLE ETTRKWAQYK QACLRDLLKE PSGIFCNGTF
101  DQYVCWPHSS PGNVSVPCPS YLPWWSEESS GRAYRHCLAQ GTWQTIENAT
151  DIWQDDSECS ENHSFKQNVD RYALLSTLQL MYTVGYSFSL ISLFLALTLL
201  LFLRKLHCTR NYIHMNLFAS FILRTLAVLV KDVVFYNSYS KRPDNENGWM
251  SYLSEMSTSC RSVQVLLHYF VGANYLWLLV EGLYLHTLLE PTVLPERRLW
301  PRYLLLGWAF PVLFVVPWGF ARAHLENTGC WTTNGNKKIW WIIRGPMMLC
351  VTVNFFIFLK ILKLLISKLK AHQMCFRDYK YRLAKSTLVL IPLLGVHEIL
401  FSFITDDQVE GFAKLIRLFI QLTLSSFHGF LVALQYGFAN GEVKAELRKY
451  WVRFLLARHS GCRACVLGKD FRFLGKCPKK LSEGDGAEKL RKLQPSLNSG
501  RLLHLAMRGL GELGAQPQQD HARWPRGSSL SECSEGDVTM ANTMEEILEE
551  SEI
```

FIG.7

CLONED GLUCAGON-LIKE PEPTIDE 2 RECEPTORS

This is a continuation-in-part application of U.S. Ser. No. 08/767,224, filed Dec. 13, 1996 now abandoned.

FIELD OF THE INVENTION

The invention is in the field of molecular biology. It relates, more particularly, to cloned glucagon-like peptide 2 receptors and their use in drug screening and related applications.

BACKGROUND TO THE INVENTION

Glucagon-like peptide-2 (GLP-2) is a 33 amino acid peptide, which is expressed in a tissue determined fashion from the pleiotrophic glucagon gene and is highly related in terms of amino acid sequence to glucagon and Glucagon-like peptide-1 (GLP-1). Mammalian forms of GLP-2 are highly conserved: for example, the human and degu (a south American rodent) forms differ by one and three amino acids respectively from rat GLP-2. Recently it was demonstrated that GLP-2 is an intestinotrophic peptide hormone; when given exogenously, GLP-2 can produce a marked increase in the proliferation of small intestinal epithelium of the test mice (Drucker et al, (1996) PNAS, 93:7911–7961). More recently, GLP-2 has been shown to increase D-Glucose maximal transport rate across the intestinal basolateral membrane. (Cheeseman and Tseng: American Journal of Physiology (1996) 271:G477–G482)

To accelerate research into gastrointestinal biology and development of drugs useful in the treatment of gastrointestinal disorders, it would be useful to provide the receptor through which the effects of GLP-2 are mediated.

SUMMARY OF THE INVENTION

The GLP-2 receptor has now been cloned and characterized. Accordingly, the present invention provides an isolated polynucleotide encoding a mammalian GLP-2 receptor, including the rat and human forms. In aspects of the invention, polynucleotide coding for the GLP-2 receptor is utilized for expression to obtain functional receptor protein and for further gene cloning to identify structurally related receptor proteins. In related aspects of the invention, antisense versions of GLP-2 receptor-encoding polynucleotides and fragments thereof are obtained and utilized to regulate GLP-2 receptor expression.

In another of its aspects, the invention provides GLP-2 receptor as a product of recombinant production in a cellular host. In related aspects, there are provided recombinant host cells that express GLP-2 receptor, as well as receptor-bearing membranes derived from such cells, and expression constructs in which polynucleotide coding for the GLP-2 receptor is linked to expression controls functional in the selected host cell.

In another of its aspects, the GLP-2 receptor is utilized in a chemicals screening program to identify GLP-2 receptor ligands. This method comprises the steps of incubating the candidate ligand with an GLP-2 receptor-producing cell of the present invention, or with a membrane preparation derived therefrom, and then assessing the interaction by determining receptor/candidate ligand binding.

In another of its aspects, the invention provides antibodies directed to the GLP-2 receptor, for use for example in diagnostic procedures.

The invention is further described with reference to the following drawings in which:

BRIEF REFERENCE TO THE DRAWINGS

FIGS. 1A and 1B disclose a cDNA sequence (SEQ ID NO: 1), nucleotides 17 to 1546 of which encode the rat GLP-2 receptor.

FIG. 2 discloses the amino acid sequence of the expression product (SEQ ID NO:2) from the cDNA of FIGS. 1A and 1B.

FIG. 3 illustrates the relative binding affinities of a GLP-2 peptide and a GLP-1 peptide for the receptor encoded by SEQ ID NO: 1.

FIG. 4 discloses a cDNA sequence of 667 nucleotides (SEQ ID NO: 9) which encodes 222 amino acids (SEQ ID NO: 10) of the human GLP-2 receptor.

FIG. 5 discloses the amino acid sequence (SEQ ID NO: 10) expressed from the cDNA of FIG. 4.

FIG. 6 discloses a cDNA sequence (SEQ ID NO: 11), nucleotides 121–1779 of which encode the human GLP-2 receptor.

FIG. 7 discloses the amino acid sequence of the expression product (SEQ ID NO: 12) from the cDNA of FIG. 6.

FIG. 8 illustrates the relative binding affinities of GLP-2 peptide and GLP-1 peptide for the receptor encoded by SEQ ID NO: 11.

DETAILED DESCRIPTION AND PREFERRED EMBODIMENTS

The invention relates in one respect to polynucleotides that code for GLP-2 receptors. Such polynucleotides may be in the form of RNA, or in the form of DNA including cDNA, genomic DNA and synthetic DNA. The GLP-2 receptors are characterized by structural features common to the G-protein coupled receptor class, including seven transmembrane regions, and by the functional properties of binding GLP-2 peptide selectively relative to GLP-1 peptide and, when expressed functionally in a host cell, of responding to GLP-2 binding by signal transduction.

The activity of a G-protein coupled receptor such as a GLP-2 receptor can be measured using any of a variety of appropriate functional assays in which activation of the receptor results in an observable change in the level of some second messenger system, such as adenylate cyclase, calcium mobilization, inositol phospholipid hydrolysis or guanylyl cyclase.

In one embodiment of the invention, the GLP-2 receptor is encoded by the polynucleotide sequence of SEQ ID NO: 1. This particular GLP-2 receptor-encoding polynucleotide, also referred to as the WBR gene, is a cDNA of rat origin. The expression product of this polynucleotide incorporates the mature form of the GLP-2 receptor, and may incorporate a secretion signal that is removed before membrane integration of the mature GLP-2 receptor product. The expressed GLP-2 receptor product (FIG. 2, SEQ ID NO: 2) is characterized structurally as a single 509 amino acid polypeptide chain having a predicted molecular weight of 59 kDa. With respect to structural domains of this GLP-2 receptor, hydropathy analysis and sequence alignment with related members of this sub-family of G protein coupled receptors indicates seven putative transmembrane domains, one spanning residues 140–162 inclusive (TM 1), another spanning residues 170–189 (TM II), a third spanning residues 221–244 (TM III), a fourth spanning residues 259–280 (TM IV), a fifth spanning 298–321 (TM V), a sixth spanning 345–364 (TM VI) and a seventh spanning 381–400 (TM VII). Based on this assignment, it is likely that this GLP-2 receptor, in its natural membrane-bound form, consists of a an N-terminal extracellular domain, followed by a hydrophobic region containing seven transmembrane domains and an intracellular 401–509 amino acid C-terminal domain. The protein exhibits the highest degree of homology to the rat GLP-1 receptor with 38% identity at the amino acid level. Yet another aspect of the invention is amino acid sequences corresponding to any of the above domains, and nucleotide sequences which encode these amino acid sequences.

Figure 3:
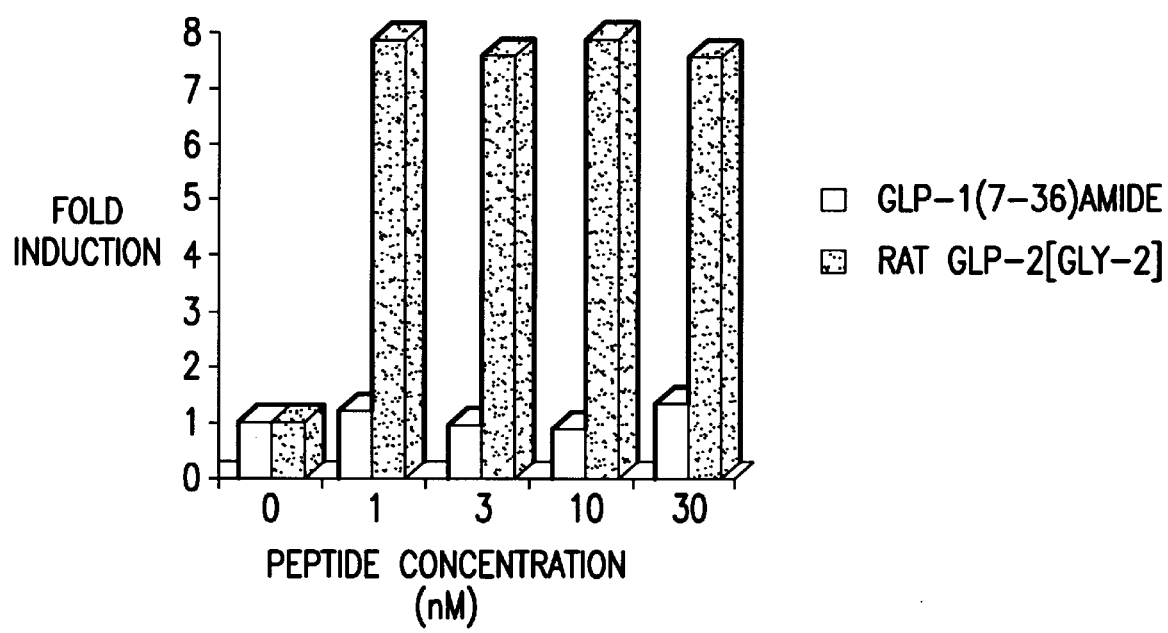
Figure 8:
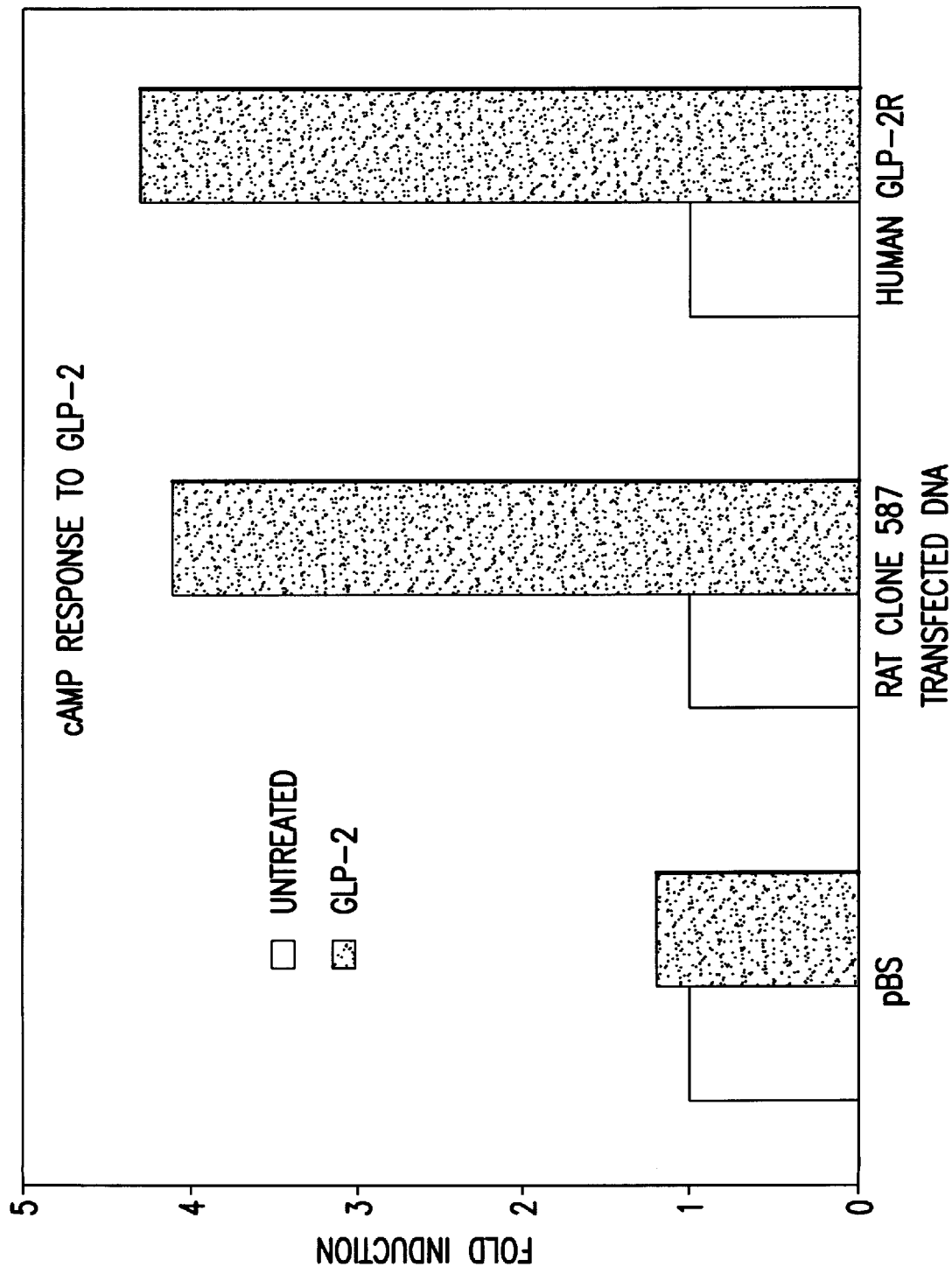

In a related embodiment, the cDNA is of human origin (FIG. 3, SEQ ID NO: 9) and encodes a protein having the amino acids of SEQ ID NO: 10. This nucleic acid was isolated using the rat cDNA sequence as described generally directly below and in detail in Example 3. In a further related embodiment of the invention, the cDNA is of human origin (SEQ ID NO: 11) and encodes the full length human GLP-2 receptor having the amino acid sequence of SEQ ID NO: 12. The human GLP-2 receptor precursor product (FIG. 7, SEQ ID NO: 12) is characterized structurally as a single 553 amino acid polypeptide chain having a predicted molecular weight of 72 kDa. With respect to structural domains of this GLP-2 receptor, hydropathy analysis and sequence alignment with related members of this sub-family of G protein coupled receptors indicates seven putative transmembrane domains, one spanning residues 181–203 inclusive (TM I), another spanning residues 211–230 (TM II), a third spanning residues 262–285 (TM III), a fourth spanning residues 300–321 (TM IV), a fifth spanning residues 339–362 (TM V), a sixth spanning residues 386–405 (TM VI), and a seventh spanning residues 422–441 (TM VII). Based on this assignment, it is likely that this GLP-2 receptor, in its natural membrane-bound form, consists of an N-terminal extracellular domain, followed by a hydrophobic region containing seven transmembrane domains interspersed with six short hydrophilic domains, and an intracellular domain, which is predicted to span residues 442–553. A second form of this GLP-2 receptor encompassed by the invention has a translational start site at the methionine codon at position 26 of the amino acid sequence presented in FIG. 7 SEQ ID No. 12. The resulting 528 amino acid polypeptide chain also consists of an extracellular domain, seven transmembrane domains, and an intracellular domain, and is at least 95% identical in sequence to residues 26–553 of the sequence presented in FIG. 7, SEQ ID NO: 12.

In another embodiment, the invention provides GLP-2 receptor polynucleotide sequences as a tool useful to identify structurally related polynucleotides. At low stringency hybridization conditions, for instance, polynucleotide libraries can be probed to identify genes that are at least about 40% homologous to the GLP-2 receptor gene. To facilitate isolation of WBR gene homologs that are also GLP-2 receptor-encoding, stringency conditions are desirably enhanced to identify homologs having at least 80% sequence identity at the polynucleotide level to WBR. More desirably the WBR gene homologs are 90% identical, and most desirably they have at least 95% sequence identity when compared to WBR. Preferably, the isolated WBR homologs are characterized in that (1) they can be amplified using the PCR primers of SEQ ID NO: 3 and SEQ ID NO: 4 and (2) they bind to the probe of SEQ ID NO: 5.

In a related embodiment the cDNA sequence of the human GLP-2 receptor can be used in appropriately labeled form for diagnosis of conditions associated with aberrant expression of the GLP-2 receptor.

In order to isolate GLP-2 receptor encoding homologs of the WBR gene, it is desirable but not necessary to use libraries of fetal or mature hypothalamal, jejunal, hindbrain or stomach tissue obtained from the vertebrate species targeted for receptor isolation. The invention accordingly includes not only the WBR but structural homologs thereof and particularly those that code for proteins having GLP-2 receptor properties. As exemplified hereinbelow, using the WBR gene as a starting material the human homolog of the rat GLP-2 receptor has now been isolated. Thus, the invention provides polynucleotides that encode GLP-2 receptors, including rat GLP-2 receptor and vertebrate homologs, particularly mammalian homologs thereof including human homologs thereof, as well as synthetic variants of these.

It will be appreciated that such homologs can also be identified in libraries by screening with fragments of the WBR gene, which incorporate at least 15 nucleotides, and preferably at least 25 nucleotides. With reference to SEQ ID NO: 1 and the nucleotide numbering appearing thereon, such nucleotide fragments include those corresponding in sequence to the extracellular GLP-2 binding domain, and the transmembrane regions.

Technically, the identification of WBR-related genes can be achieved by applying standard hybridization or amplification techniques to a tissue-derived polynucleotide library. A wide variety of such libraries are commercially available. Where construction of a cDNA library is necessary, established techniques are applied. For example, isolation of such a WBR homolog typically will entail extraction of total messenger RNA from a fresh source of tissue, such as hypothalamal, jejunal, stomach or hindbrain tissue, preferably hypothalamal tissue, followed by conversion of message to cDNA and formation of a library in for example a bacterial plasmid, more typically a bacteriophage. Such bacteriophage harboring fragments of the DNA are typically grown by plating on a lawn of susceptible *E. coli* bacteria, such that individual phage plaques or colonies can be isolated. The DNA carried by the phage colony is then typically immobilized on a nitro-cellulose or nylon-based hybridization membrane, and then hybridized, under carefully controlled conditions, to a radioactively (or otherwise) labelled probe sequence to identify the particular phage colony carrying the fragment of DNA of particular interest, in this case a WBR homolog. The phage carrying the particular gene of interest is then purified away from all other phages from the library, in order that the foreign gene may be more easily characterized. Typically, the gene or a portion thereof is subcloned into a plasmidic vector for convenience, especially with respect to the full determination of its DNA sequence.

As an alternative to obtaining GLP-2 encoding DNA directly as a DNA insert from an available or a constructed cDNA library, in light of the present disclosure it can be synthesized de novo using established techniques of gene synthesis. Because of the length of the GLP-2 receptor-encoding DNAs of SEQ ID NO: 1, SEQ ID NO: 9 and SEQ ID NO: 11, application of automated synthesis may require staged gene construction, in which regions of the gene up to about 300 nucleotides in length are synthesized individually and then ligated in correct succession for final assembly. Individually synthesized gene regions can be amplified by PCR. The application of automated synthesis may typically be applied by synthesizing specific regions or fragments of the gene and ligating them, usually via designed overlaps, in correct succession to form the final gene sequence. In this case, the longer the oligonucleotide building blocks, the fewer will be the ligations needed, resulting in greater ease of assembly.

The application of automated gene synthesis techniques provides an opportunity for generating sequence variants of the naturally occurring GLP-2 receptor gene. It will be appreciated, for example, that polynucleotides coding for the GLP-2 receptor herein described can be generated by substituting synonymous codons for those represented in the naturally occurring polynucleotide sequences herein provided. In addition, polynucleotides coding for synthetic variants of the GLP-2 receptor herein provided can be generated which incorporate from 1 to 20, e.g., from 1 to 5, amino acid substitutions, or deletions or additions. Since it will be desirable typically to retain the natural ligand binding profile of the receptor for screening purposes, it is desirable to limit amino acid substitutions, for example to the so-called conservative replacements in which amino acids of similar charge are substituted, and to limit substitutions to those sites less critical for receptor activity. For example, substitution of nucleotides "G" and "A" for nucleotides "A" and "G" respectively at positions 374 and 375 of the human cDNA sequence of SEQ ID NO: 11; resulting in the replacement of the naturally occurring arginine residue at position 85 of SEQ ID NO: 12 with a glutamic acid residue, provides a functional receptor. This functional receptor is referred to herein as the cloned residue 85 variant human GLP-2 receptor.

Having obtained GLP-2 receptor encoding polynucleotide, GLP-2 receptor can be produced in a number of ways, including in vitro transcription and via incorporation of the DNA into a suitable expression vector and expression in the appropriate host, for example a bacteria such as *E. coli*, yeast or a mammalian cell. A variety of gene expression systems have been adapted for use with these hosts and are now commercially available, and any one of these systems can be selected to drive expression of the GLP-2 receptor-encoding DNA. Expression vectors may be selected to provide transformed cell lines that express the receptor-encoding DNA either transiently or in a stable manner. For transient expression, host cells are typically transformed with an expression vector harboring an origin of replication functional in a mammalian cell. For stable expression, such replication origins are unnecessary, but the vectors will typically harbor a gene coding for a product that confers on the transformants a survival advantage, to enable their selection such as a gene coding for neomycin resistance in which case the transformants are plated in medium supplemented with neomycin.

These expression systems, available typically but not exclusively in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which the receptor-encoding DNA is linked with expression controlling DNA sequences recognized by the host, and which include a region 5' of the receptor-encoding DNA to drive expression, and a 3' region to terminate expression.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metallothionein gene promoter, and other steroid-inducible promoters.

In another of its aspects, the invention provides cells or membranes derived therefrom which are adapted by genetic alteration for use, for example, in identifying GLP-2 receptor ligands. In preferred embodiments, such cells are adapted genetically by the insertion of polynucleotide coding for a GLP-2 receptor. In particularly preferred embodiments, such cells incorporate a recombinant DNA molecule, e.g. an expression construct/vector, in which DNA coding for the GLP-2 receptor and expression controlling elements functional in the host are linked operably to drive expression of the DNA. For incorporation of receptor into cell plasma membranes, the vector can be designed to provide a suitable heterologous signal peptide sequence if the naturally occurring signal peptide is not encoded within the receptor DNA.

Suitable GLP-2 producing cells include the Chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

For use in ligand screening assays, cell lines expressing the receptor-encoding DNA can be stored frozen for later use. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purpose, i.e., ligand binding experiments, frozen intact cells are homogenized while in cold water suspension and a membrane pellet is collected after centrifugation. The pellet is then washed in cold water, and dialyzed to remove any endogenous GLP-2 receptor ligands that would otherwise compete for binding in the assays. The dialyzed membranes may then be used as such, or after storage in lyophilized form, in the ligand binding assays.

The binding of a candidate ligand to a selected GLP-2 receptor of the invention is performed typically using a predetermined amount of cell-derived membrane (measured for example by protein determination), generally from about 25 ug to 100 ug. Generally, competitive binding assays will be useful to evaluate the affinity of a test compound relative to GLP-2. This competitive binding assay is performed by incubating the membrane preparation with radiolabelled GLP-2 peptide, for example [$^3$H]-GLP-2 or a radioiodinated GLP-2 analog, in the presence of unlabelled test compound added at varying concentrations. Following incubation, either displaced or bound radiolabelled GLP-2 can be recovered and measured, to determine the relative binding affinities of the test compound and GLP-2 for the GLP-2 receptor used as substrate. In this way, the affinities of various compounds for the GLP-2 receptor can be measured.

Alternatively, intact, fresh cells, harvested about two days following after transient transfection or after about the same period following fresh plating of stably transfected cells, can be used for ligand binding assays by the same methods as used for membrane preparations. In this case, the cells must be harvested by more gentle centrifugation so as not to damage them, and all washing must be done in a buffered medium.

As an alternative to using cells that express receptor-encoding DNA, ligand characterization may also be performed using cells for example Xenopus oocytes, that yield functional membrane-bound receptor following introduction of messenger RNA coding for the GLP-2 receptor. In this case, the GLP-2 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Each oocyte is a single cell, but is large enough to be penetrated by a fine-tipped microneedle without causing irreparable damage. Following the injection of nL volumes of an RNA solution, the oocytes are left to incubate for up to several days, whereupon the oocytes are tested for the ability to respond to a particular ligand molecule supplied in a bathing solution.

Candidate GLP-2 receptor ligands can vary widely in structure, and include proteins which are highly related to GLP-2 itself in terms of amino acid sequence. For instance, the peptides disclosed in co-pending U.S. patent application Ser. Nos. 08/422,540 and 08/631,273, now abandoned, incorporated herein by reference, may usefully be screened for GLP-2 receptor binding activity. Furthermore, the advent of high throughput screening makes feasible the screening of a chemical library containing hundreds or thousands of test compounds for GLP-2 receptor binding activity.

In addition to using the receptor-encoding DNA to construct cell lines useful for ligand screening, expression of the DNA can according to another aspect of the invention be performed to produce fragments of the receptor in soluble form, for structure investigation, to raise antibodies and for other experimental uses. It is expected that the portion of the GLP-2 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor.

To accomplish this, the full-length GLP-2 receptor-encoding DNA may be modified by site-directed mutagenesis, so as to introduce a translational stop codon into the extracellular N-terminal region, immediately before the sequence encoding the first transmembrane domain (TM1), i.e., before residue 140 of SEQ ID NO: 2 and before residue 181 of SEQ ID NO: 12. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf 9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the GLP-2 receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location, for example in intestinal tissue, the present invention also provides, in another of its aspects, labelled antibody to a GLP-2 receptor. To raise such antibodies, there may be used as immunogen either the intact, soluble receptor or an immunogenic fragment thereof, produced in a microbial or mammalian cell host as described above or by standard peptide synthesis techniques. Regions of the GLP-2 receptor particularly suitable for use as immunogenic fragments include those corresponding in sequence to an extracellular region of the receptor, or a portion of the extracellular region, such as peptides consisting of 10 or more amino acids of the 401–509 region of SEQ ID NO: 2. With regard to the human GLP-2 receptor (SEQ ID NO: 12), peptides comprising the mature extracellular domain (residues 65–180); intracellular loop 3 (resides 363–385) and the intracellular C-terminal domain (residues 442–533) may be usefully employed as immunogens for the production of antibodies to the human GLP-2 receptor.

Antibodies to the desired GLP-2 receptor or fragment immunogen are available, for polyclonal antibody production, from the blood of an animal that has been immunized with the immunogen. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

Animal model systems which elucidate the physiological and behavioral roles of the GLP-2 receptor are produced by creating transgenic animals in which the activity of the GLP-2 receptor is either increased or decreased, or the amino acid sequence of the expressed GLP-2 receptor is altered, by a variety of techniques. Examples of these techniques include, but are not limited to: 1) Insertion of normal or mutant versions of DNA encoding a GLP-2 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these GLP-2 receptor sequences. The technique of homologous recombination is well known in the art. It replaces the native gene with the inserted gene and so is useful for producing an animal that cannot express native GLP-2 receptors but does express, for example, an inserted mutant GLP-2 receptor, which has replaced the native GLP-2 receptor in the animal's genome by recombination, resulting in underexpression of the transporter. Microinjection adds genes to the genome, but does not remove them, and so is useful for producing an animal which expresses its own and added GLP-2 receptors, resulting in overexpression of the GLP-2 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a GLP-2 receptor is cesium chloride purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplary purposes.

The invention having been described above, may be better understood by referring to the following examples. The following examples are offered for the purpose of illustrating the invention and should not be interpreted as a limitation of the invention.

EXAMPLE 1

Isolation of the GLP-2 Receptor
PCR-Assisted Cloning of Partial Rat and Mouse GLP-2 Receptor cDNAs Rat Neonate Intestine cDNA library (Stratagene, La Jolla, Calif.; Cat. 936508) and Mouse Jejunum first strand cDNA was prepared. Degenerate primers M-2F/S (SEQ ID NO: 3) and M-7R/S (SEQ ID NO: 4) were used to amplify a partial fragment of the rat GLP-2 receptor from the Rat Neonate Intestine cDNA library and of the mouse GLP-2 receptor from Mouse Jejunum template. The protocol is described below:

Degenerate PCR
6 $\mu$l 10× VENT buffer from New England Biolabs
6 $\mu$l 2.5 $\mu$M each stock dATP, dCTP, dGTP and dTTP
4 $\mu$l rat neonate intestine cDNA (1:10 dilution)
3 $\mu$l 25 $\mu$M primer [5'-TTTTTCTAGAASRTSATSTACACNGTSGGCTAC-3'] (SEQ ID NO: 3)
3 $\mu$l 25 $\mu$M primer [5'-TTTTCTCGAGCCARCARCCASSWRTARTTGGC-3'] (SEQ ID NO: 4)
2 $\mu$l (10 units) Amplitaq DNA polymerase (Perkin Elmer)
36 $\mu$l ddH$_2$O.

Reaction conditions: 35 cycles at 94° C., 2° min.; 94° C., 1 min.; 53° C., 30 sec.; 72° C., 1 min.

The predominant PCR product was a 303 base pair (bp) DNA fragment. 30 $\mu$l samples of the above PCR were purified using the QIAGEN PCR purification kit and eluted in 30 $\mu$l ddH$_2$O.

Reamplification PCR
6 $\mu$l 10× VENT buffer from New England Biolabs
6 $\mu$l 2.5 $\mu$M each stock dATP, dCTP, dGTP and dTTP
4 $\mu$l above purified PCR template
3 $\mu$l 25 $\mu$M primer [5'-TTTTTCTAGAASRTSATSTACACNGTSGGCTAC-3'] (SEQ ID NO: 3)
3 $\mu$l 25 $\mu$M primer [5'-TTTTCTCGAGCCARCARCCASSWRTARTTGGC-3'] (SEQ ID NO: 4)
2 $\mu$l (10 units) Amplitaq DNA polymerase (Perkin Elmer)
36 $\mu$l ddH$_2$O Reaction conditions: 31 cycles at 94° C., 2 min.; 94° C., 1 min.; 53° C., 30 sec.; 72° C., 1 min.

The predominant product at 303 base pair (bp) was cut out and purified using QIAGEN QIAquick gel purification protocol into 30 $\mu$l ddH2O.

Next, double digest (Xba I and Xho I) was done on the entire reamplified PCR reaction as follows:
28 $\mu$l DNA
16 $\mu$l 10× One-Phor-All buffer (Pharmacia)
2 $\mu$l (40 units) Xba I enzyme (Pharmacia)
2 $\mu$l (40 units) Xho I enzyme (Pharmacia)
30 $\mu$l ddH$_2$O.

The samples were digested 4 hours in 37° C. water block heater, brought up to 100 $\mu$l volume with ddH$_2$O (sterile) and purified by (1) equal amount (100 ul) chloroform extraction; (2) weekend precipitation with 2 volumes ethanol/10 volumes 3M sodium acetate; (3) 1× wash with 70% EtOH; and (4) resuspension in 10 $\mu$l 1× TE (pH 8.0).

pBluescript clone 5HT1F#9 was next digested with Xba I and Xho I as follows:
10 $\mu$l DNA (pBluescript clone 5HT1F#9)
5 $\mu$l 10× NEBuffer 2 (New England Biolabs)
3 $\mu$l (1:20 dilution=3 units) Xba I (New England Biolabs)
3 $\mu$l (1:20 dilution=3 units) Xho I (New England Biolabs)
5 $\mu$l (10×) BSA (New England Biolabs)
24 $\mu$l ddH$_2$O.

The sample was digested for 3 hours in 37 C. water block heater, heat-inactivated at 65 C. for 20 min and purified using GeneCleanII kit from BIO 101. Aliquots of the PCR reactions were cloned into the above pBluescript plasmid vector using T4 DNA ligase kit (New England Biolabs) and transformed into Epicurean Coli XL-2 Blue MRF' Ultracompetent cells (Stratagene). The transformation was plated onto 2×YT+AMP plates and single colonies were picked. DNA minipreps were made using QIAGEN QIA-prep 8 miniprep kit and the sequences of the fragments were determined using ABI system. Novel sequences were identified containing a partial fragment of the rat and mouse GLP-2 receptor sequence.

Cloning of cDNA with complete GLP-2 receptor coding region was achieved as follows: First, cDNA libraries from the following three tissues were used for screening,
1. Rat Hypothalamus (RHT)
2. Rat Hind Brain (RHB)
3. Rat Duodenum and Jejunum (RDJ)

The three cDNA libraries were prepared by priming with random primer and subcloning unidirectionally into Hind III and Not I sites of pcDNA3.

Next, the three cDNA libraries were homology screened by a degenerate oligo C4-4 [5'-AACTACATCCACMKGMAYCTGTTYVYGTCBTTCAT SCT-3'] (SEQ ID NO: 5) by colony lifts and filter hybridization. The following hybridization conditions were employed: 5× SSPE (1× SSPE is 0.18M NaCl, 10 mM NaH$_2$PO$_4$ (pH 7.4), 10 mM EDTA (pH 7.4)) and 5× Denharts solution (1% Ficoll, 1% Polyvinylpyrrolidone, 1% BSA); 25 mg/ml salmon sperm DNA.

Filters were hybridized at 50° C. overnight. Then the filters were washed 2 times in 2× SSPE and 1% SDS at room temperature for 30 min, 2 times in 2× SSPE and 1% SDS at 50° C. for 20 min per wash, and finally two times in 1× SSPE and 0.5% SDS. Positive clones were identified by autoradiography. A plug of 1 cm$^2$ surrounding the positive clone was removed from the plate and placed in 1 ml of 2× YT+20% Glycerol, vortexed and was frozen at −80° C.

Plasmid DNA from positive plugs was prepared as follows: 100 ml of bacterial culture of each positive plug was grown on an agar plate. The bacterial cells were scraped and resuspended in 1 ml of 2×YT medium+20% Glycerol. Bacterial pellet from the 250 ml of bacterial resuspension was resuspended in 150 ml of Solution I (50 mM Glucose, 10 mM Tris-HCl, 1 mM EDTA), lyse in Solution II (0.2M NAOH, 1% SDS), neutralized with ice cold Solution III (Potassium acetate; 4 vol. of 5M potassium acetate+1 vol. of 10M acetic acid). After pelleting bacterial DNA, 340 ml isopropanol was added to the supernatant. This was centrifuged at max for 15 min. The pellet was resuspended in TE+20 mg/ml RNase, incubated at 37 C. for 30 minutes and precipitated with isopropanol+0.2M potassium acetate. After centrifugation, the pellet was washed with 70% alcohol, allowed to air dry and resuspended in TE.

Plasmid DNA from 2777-clone pools of rat hypothalamus cDNA library RHT cDNA library was next exploited as follows: Two primers were designed from an area of the PCR-cloned GLP-2 receptor cDNA sequence that did not have identity to known receptors of the gene family. The two primers P23-R1 and P23-F1 amplified a 196 bp fragment only from novel clone DNA but not with GLP-1 receptor cDNA or PACAP receptor cDNA. The Expand™ PCR system from Boehringer Mannheim (Cat. 1681-842) was used under the following conditions:

2 µl of 10× Expand™ Buffer 1
2.8 µl of 2.5 mM dNTP mix
0.6 µl of primer P23-R1 [5'-TCATCTCCCTCTTCTTGGCTCTTAC-3'] (SEQ ID NO: 6)
0.6 µl of primer P23-F1 [5'-TCTGACAGATATGACATCCATCCAC-3'] (SEQ ID NO: 7)
0.3 µl of Expand PCR enzyme (1 unit)
12.7 µl water
1 µl DNA Reaction conditions: 32 cycles at 93° C., 40 sec; 58° C., 40 sec; 68° C., 40 sec.

DNAs from each positive plug or pool of 2777-clone pools were amplified with specific primers P23-F1 and P23-R1 under the conditions specified above. Out of 1057 C4-4 hybridization-positive plugs and 884 2777-clone pools only five template sources amplified a 196 bp PCR product. These were: (1) Plug 334, (2) Plug 780, (3) RHT pool 233, (4) RHT pool 440, and (5) RHT pool 587.

Amplification of GLP-2R cDNA from the five positive templates was then performed. By using one specific primer (P23-R1 or P23-F1) and one primer based on pcDNA3 vector (Invitrogen) sequence (830F or 1186R), the GLP-2R cDNA insert was directly amplified from clonally impure plugs or 2777-clone pools. The sequences of the vector primers were as follows:

830F: [5'-AACCCACTGCTTAC-3'] (SEQ ID NO: 13)

1186R: [5'-CCCAGAATAGAATGACACC-3'] (SEQ ID NO: 14)

The PCR was done under the following conditions using Expand™ PCR system from Boehringer Mannheim (Catalogue no. 1681-842).

2 µl of 10× Expand™ Buffer 1
2.8 µl of 2.5 mM dNTP mix
0.6 µl of Primer 1
0.6 µl of Primer 2
0.3 µl of Enzyme (1 unit)
12.7 µl water
1 µl DNA Reaction conditions: 32 cycles at 93° C., 45 sec; 50° C., 45 sec; 68° C., 1 min.

The most prominent band was reamplified, purified and sequenced. Based on the amplified sequence obtained, additional primers were designed and new sequencing carried out. In this manner the complete sequences of the GLP-2R cDNA inserts in all five sources of clones were determined. Sequence analysis showed that only pool RHT 440 and pool RHT 587 contain clones with complete coding sequence of GLP-2R and that the two clones were identical (derived from the same cDNA clone).

Because of difficulty in clonally purifying the GLP-2 receptor cDNA clone from the RUT 440 or RHT 587 cDNA library pools, the cDNA was amplified and recloned into pcDNA3. Based on the sequence obtained from RHT 440 and RHT 587, two primers were designed adjacent to the 5' and 3' ends of the coding region.

WBR-C5: [5'-CAGGGGCCGGTACCTCTCCACTCC-3'] (SEQ ID NO. 15)

WBR-C3: [5'-TTGGGTCCTCGAGTGGCCAAGCTGCG-3'] (SEQ ID NO. 16)

The two primers were used to amplify a DNA fragment of approximately 1525 bp fragment under the following PCR conditions using Expand™ PCR system from Boehringer Mannheim (Catalogue no. 1681-842).

10 µl of 10× Expand™ PCR Buffer 1
14 µl of 2.5 mM dNTP mix
3.0 µl of Primer 1 (10 µM)

3.0 μl of Primer 2 (10 μM)
1.5 μl of Enzyme (5 units)
63.5 μl water
5 μl DNA

Reaction conditions: 5 cycles (93° C., 1 Min; 72° C., 40 s; 60° C., 45 sec; 68° C., 2 min) 25 cycles (93° C., 1 min; 72° C., 1 min; 68° C., 2 min).

The amplified product was subcloned into Kpn I and Xho I sites of pcDNA3 vector (Invitrogen). Plasmid DNA was prepared using the method described above.

EXAMPLE 2

Ligand Binding Assay

Cos-1 cells were transfected as described in Analytical Biochemistry, 218:460–463(1994) with Rat clone 587 GLP-2 receptor, cloned human GLP-2 receptor, or cloned residue 85 variant human GLP-2 receptor. Rat GLP-1 (7–36) amide was used as a control peptide. Solutions used were as follows: RSC in RPMI 1640 (49 ml RPMI+1 ml FCS+50 ul chloroquine, 100 mM); DEAE/RSC Solution: 18.4 ml RSC+ 1.6 ml DEAE/Dextran (10 mg/ml).

The assay procedure entailed the following:

a) 50 mg of either rat clone 587 GLP-2 receptor, or cloned human GLP-2 receptor, or cloned residue 85 variant human GLP-2 receptor was added to a 50 ml tube containing six mls. of RSC and incubated at 37° C.

b) Six ml of DEAE/RSC solution was added to each tube and incubate at 37° C. for 2 min.

c) 1.5 ml of COS-1 cell suspension (5.5 millions cells) was added to each tube and incubated for 1 hr 45 min at 37° C.

d) Following incubation, the sample was spun for 5 minutes at low speed, washed with DMEM/F12+10% FBS twice, and the pellet resuspended in 12.5 ml DMEM/F12+10% FBS media.

e) One ml of cell suspension (step d) was added to each well of 6 well plates coated with poly-D-lysine (from Collaborative Biomedical), containing 3 ml of media (0.45 million cells/well).

f) Plates were incubated at 37° C. for 3 days.

Treatment of Transfected Cos-1 cells with GLP-1/GLP-2 analog was done as follows: Solutions: DMEM/F12 (SFM)+ IBMX (3-isobutyl-1-methylxanthin) 0.85 mM+0.1% ascorbic acid and 10 um pargyline (all solutions purchased from Sigma). Media was prepared fresh on day of use. Assay Procedure: The culture media of each well (transfected 6 well plates, cells) was removed, and the wells were washed once with SFM media. Then 2 ml of SFM+IBMX media was added to each well and plates were incubated at 37° C. for 10 min. Following incubation, the SFM+IBMX was removed from each well and fresh SFM+IBMX media containing GLP-1/GLP-2 (GLP-1,7-36,amide from Sigma, [Gly2]hGLP-2 from Allelix) concentration 1, 3, 10 and 30 nM were added to the appropriate wells. Plates incubated at 37° C. incubator for 30 min. Following incubation, the media were removed from each well. The wells were washed once with 1 ml PBS (Phosphate Buffered Saline). Each well was then treated with 1 ml cold 95% ethanol:5 mM EDTA (2:1) at 4° C. for 1 hr. Cells from each well then were scraped and transferred into individual eppendorf tubes. Tubes were centrifuged for 5 min at 4° C., and the supernatants were transferred to new eppendorf tubes and dried in speed vacuum. Following drying, tubes were reconstituted in 100 ul of Na— Acetate and kept at 4° C., 25 μl of this solution used for cAMP Assay.

The functional assay was performed as follows: cAMP content for each extract was determined in duplicate by EIA (Enzyme ImmunoAssay) using the Amersham Biotrak cAMP EIA Kit (Amersham 225). Results of the assays, illustrated in FIG. 3 and FIG. 6, demonstrate the GLP-2 selectivity exhibited by the cloned rat and human receptors. In a similar assay of binding to the GLP-1 receptor, the expected pattern of binding preferentially to GLP-1 was observed.

EXAMPLE 3

Isolation Of Human GLP-2 Receptor cDNA

Medium-Stringency Hybridization Screening of a Human Hypothalamus cDNA Library

One million clones from a λgt10 cDNA library from human hypothalamus (Clontech; Cat. No. 1172a) were screened by plaque lifts on nitrocellulose filters (Amersham; Cat.RPN137E). The probe was prepared by random primer labeling a DNA fragment containing the complete coding region of rat GLP-2 receptor. The DNA fragment was isolated from clone 587-C1, which contains the complete coding region from SEQ ID NO: 2.

Pre-hybridization and hybridization were each carried out overnight in a hybridization solution consisting of 50% formamide, 5× SSPE, 5× Denhart's solution, 0.5% SDS and salmon sperm DNA (200 mg/ml). After hybridization the filters were washed under the following conditions (medium stringency):

two times at room temperature in 2× SSPE and 0.01% SDS.

two times at 42° C. in 2× SSPE and 0.01% SDS.

two times at 42° C. in 0.2× SSPE and 0.01% SDS.

The filters were autoradiographed and agar plugs, each containing numerous bacteriophage plaques, were picked from regions on the plates corresponding to positive signals on the filter. From one million cDNA clones sampled in the first round screen, we identified two positive clones (HHP6-1 and HHP13). On secondary screening only HHP13 turned out positive. Several positive plaques (HHS13) from the HHP13 plate were pooled and taken for tertiary screening. Three single positive plaques from this round of screening were picked (HHT13-1, HHT13-2, HHT13-3).

PCR amplification was then used for partial sequencing of the positive clones. On a lawn of bacterial cells (*E. coli* C600Hfl), 10 ml of phage suspension from each clone was applied at marked spots. After 5 hr incubation at 37° C., the phage plaques were clearly visible and covered ~1 cm². A portion of each plaque was transferred to 200 ml of water. The samples were incubated in a boiling water bath for 5 min and centrifuged at room temperature for 10 min. One milliliter of sample was used for PCR amplification with two sets of degenerate primers:

M2FS[5'-TTTTTCTAGAASRTSATSTACACNGTSGGCTAC-3'] (SEQ ID NO: 3)

and

M7RS[5'-TTTCTCGAGCCARCARCCASSWRTARTTGGC-3'] (SEQ ID NO: 4);

-continued or

C4-4[5'-AACTACATCCACMKGMAYCTGTTYVYGTCBTTCATSCT-3'] (SEQ ID NO: 5)

and

C9-2R [5'-TCYRNCTGSACCTCMYYRTTGASRAARCAGTA-3'] (SEQ ID NO: 8).

The Expand™ PCR system from Boehringer Mannheim (Cat. 1681-842) was used under the following conditions:
5 µl of 10× Expand™ Buffer 3
7 µl of 2.5 mM dNTP mix
1.5 µl of primer M2FS or C4-4
1.5 µl of primer M7RS (with M2FS) or C9-2R (with C4-4)
0.75 µl of Expand PCR enzyme (1 unit)
33.25 µl water and
1 µl DNA.

Reaction conditions were: 32 cycles at 93° C., 1 min; 50° C., 1 min; 45° C., 1 min; 2 min.

M2FS and M7RS amplified a DNA fragment of about 300 bp and C4-4 and C92-R amplified a DNA fragment of about 700 bp. The PCR products were purified using the QIAGEN QIAquick PCR purification kit (Cat. 28104) and eluted in 50 µl 10 mM Tris, pH 8.0. Sequence analysis of the products revealed no differences between the templates, as expected from the fact that they represent multiple copies of a single cDNA clone (HHT13).

A number of factors indicate that this clone contains coding sequence of the human GLP-2 receptor. Once factor is the degree of sequence similarity. The glucagon receptor cDNA can be used to predict the expected degree of sequence conservation found between rat and human receptors. At the nucleotide level, there is 82.6% identity within the coding regions of the rat and human glucagon receptors. At the amino acid level, there is 80.9% identity and 89.1% amino acid similarity between the glucagon receptors of the two species.

In the case of the human GLP-2 receptor cloned herein, the sequence of the partial human GLP-2 receptor cDNA (HHT13) is highly homologous to rat GLP-2 receptor cDNA at both the nucleotide and amino acid level. SEQ ID NO: 9 shows 87.1% identity with the rat GLP-2 receptor cDNA sequence. The predicted amino acid sequence of this cDNA region has 87.4% identity and 93.2% similarity with the predicted amino acid sequence of the rat GLP-2 receptor. The total predicted length of the rat receptor preprotein is 509 amino acids, suggesting we have determined the sequence of about 44% of the coding region of the human receptor. The comparison of the predicted partial human sequence with the predicted amino acid sequence of rat GLP-2 receptor shows beyond a reasonable doubt that this cDNA encodes the human counterpart of the rat receptor.

Further evidence supporting this conclusion comes from a comparison of the partial human GLP-2 receptor amino acid sequence with the rat GLP-2 receptor and the 3 next closest family members, shown below:

| Receptor Sequence (amino acid) | Percent Identity with HHT13 | Percent Similarity |
|---|---|---|
| GLP-2 receptor (rat) | 87.4 | 93.2 |
| GLP-1 receptor (rat) | 50.0 | 74.1 |

-continued

| Receptor Sequence (amino acid) | Percent Identity with HHT13 | Percent Similarity |
|---|---|---|
| Glucagon receptor (rat) | 51.4 | 73.9 |
| GIP receptor (rat) | 50.7 | 70.3 |

These comparisons, together with the benchmark provided by sequence similarities between the rat and human glucagon receptors, provide definitive evidence that the cDNA designated HHT13 represents the human counterpart of the rat GLP-2 receptor.

The full amino acid sequence of the human GLP-2 receptor is obtained by first determining the sequence of the complete cDNA inserts in HHT13-1, HHT13-2 and HHT13-3. By using degenerate primers for PCR amplification and subsequent sequencing, we obtained sequence from only part of each insert. It is possible that these identical clones contain an insert which spans the complete coding sequence of the human GLP-2 receptor preprotein. To determine the complete sequence of the cDNA insert, the clones are grown in large quantity to prepare approximately 20 mg of each equivalent clone. The complete cDNA insert is excised by restriction with Eco RI, and subcloned into pcDNA3 (Invitrogen). Alternatively, two primers from vector sequence flanking the insert are used to amplify the complete cDNA insert using the Expand™ PCR system from Boehringer Mannheim (Cat. 1681-842). The amplified cDNA is cut with appropriate restriction enzymes and is subcloned into pcDNA3 (Invitrogen).

If a complete coding sequence is not present in the HHT13 clones, cDNA libraries are screened for additional clones to complete the coding region of human GLP-2 receptor cDNA. Preferably human cDNA libraries (from Stratagene or Clontech) representing the following tissues are used for screening: Human hypothalamus; Human fetal brain; Human duodenum and jejunum; Human stomach; and Human fetal intestine.

Two PCR primers are designed from the sequence of human GLP-2 receptor cDNA already determined. These primers are designed such that they could not amplify any related gene family members other than the GLP-2 receptor cDNA itself. A dilution of the cDNA library stock is used to make library sub-pools such that 50,000 clones are represented in each pool. PCR is conducted with the GLP-2 receptor-specific primers to diagnose pools containing a GLP-2 receptor cDNA clone, using the Expand™ PCR system from Boehringer Mannheim (Cat. 1681-842) under the following conditions:
2 µl of 10× Expand™ Buffer 1
2.8 µl of 2.5 mM dNTP mix
0.6 µl of primer P1
0.6 µl of primer P2
0.3 µl of Expand PCR enzyme (1 unit)
12.7 µl water
1 µl of library pool containing 50,000 clones Reaction conditions: 32 cycles at 93° C., 40 sec; 50–58° C., 40 sec; 68° C., 40 sec.

Sequence is then obtained from the complete GLP-2 receptor cDNA insert from a positive pool. By using one specific primer and one primer based on vector sequence close to the cloning site, the GLP-2 receptor cDNA insert is directly amplified from clonally impure clone pools, using the Expand™ PCR system from Boehringer Mannheim (Catalogue no. 1681-842) most suitably under the following conditions:
2 μl of 10× Expand™ Buffer 1
2.8 μl of 2.5 mM dNTP mix
0.6 μl of Primer 1
0.6 μl of Primer 2
0.3 μl of Enzyme (1 unit)

```
GT10-5KXb [5'-GGGTAGTCGGTACCTCTAGAGCAAGTTCAGCC-3'] (SEQ ID NO: 17)

vs

GT10-3BXh [5'-ATAACAGAGGATCCTCGAGTATTTCTTCCAG-3' (SEQ ID NO: 18)
```

12.7 μl water
1 μl of library pool stock

Reaction conditions: 32 cycles at 93° C., 45 sec; 50° C., 45 sec; 68° C., 1 min.

The reaction is run on a preparative agarose gel, and the most prominent band is purified and sequenced. Based on the amplified sequence obtained, additional primers are designed to obtain sequence and clones of complete coding region and clone the complete cDNA 5' RACE and 3' RACE are used to obtain complete coding sequence of the human GLP-2 receptor cDNA. Rapid Amplification of cDNA Ends (RACE) is a procedure routinely used for amplification of DNA sequences from first cDNA strand (easily prepared from mRNA) template between a defined internal site and either 3' or the 5' end of the mRNA. Total or mRNA from different human tissues are commercially available from Clontech. The 3' RACE System (Gibco-BRL Life Technologies; Cat. 18373-019) and 5' RACE System (Cat. 18374-058) kits are used. The manuals of these two products provide detailed protocols. In brief, protocols are as described below.

For the 3' RACE procedure, first strand cDNA synthesis is initiated at the poly (A) tail of mRNA using the adapter primer (provided with system) incorporating a unique sequence for universal PCR amplification of the RACE products. After synthesis of the first strand cDNA from this primer, the original mRNA template is destroyed with RNase H. Amplification is then performed using two primers: one is a gene-specific primer (which will be designed from the available partial cDNA sequence of HHT13); the other is the universal amplification primer provided with the kit. The amplified product is subcloned into a plasmid vector for sequencing.

For the 5' RACE System, the first strand cDNA is synthesized from mRNA using a gene-specific primer (which is based on the available partial cDNA sequence of HHT13) and SuperScript II reverse transcriptase. The original mRNA template is removed by treatment with RNase H. Unincorporated dNTPs, primer, and proteins are separated from cDNA using spin cartridge. A homopolymeric dCTP tail is then added to the 3'-end of the first strand cDNA using TdT enzyme and dCTP nucleotides. PCR amplification is performed using two primers: one is a nested, gene-specific primer designed from the available partial DNA sequence of HHT13; and the other is an "anchor primer" provided with the system. Both primers incorporate restriction sites for subcloning into plasmids and subsequent sequencing.

Sub-cloning of HHT13 λgt10 Clones into pcDNA3, their Sequencing and Expression

A. Amplification of cDNA Inserts with λgt10 Primers

On a lawn of bacterial cells (*E. coli* C600Hfl), 10 μl of phage resuspension from each clone was placed at marked spots. After 5 hr incubation at 37° C., the phage plaques were clearly visible. The surface of each plaque was transferred to 200 μl of water. The samples were kept in boiling water bath for 5 minutes and centrifuged at room temperature for 10 minutes. 1 μl of sample was used to amplify with a set of λgt10 primers.

The Expand™ PCR system from Boehringer Mannheim (Cat. 1681-842) was used under the following conditions:
5 μl of 10× Expand Buffer 3
7 μl of 2.5 mM dNTP mix
1.5 μl of primer GT10-5KXb
1.5 μl of primer GT10-3BXh
0.75 μl of Expand PCR enzyme (1 unit)
33.25 μl water
1 μl DNA Reaction conditions: 5 cycles of 93° C.—40 sec; 50 ° C.—1 min; 68° C.—2 min and 30 cycles of 93° C.—40 sec; Ramp to 68° C.—1 min; 68° C.—2 min.

An amplified DNA fragment of about 2200 bp long was seen on the agarose gel from all three clones. The PCR product were purified using the QIAGEN's QIAquick PCR purification kit (Cat. no. 28104) and eluted in 50 μl 10 mM Tris, pH 8.0. The templates were sequenced.

B. Subcloning into pcDNA3 Vector

The amplified and purified DNA from the three clones was restricted with Kpn I and Xho I and subcloned into pcDNA3 restricted with similar restriction enzymes. The plasmids were named pHHT13-1, pHHT13-2, and pHHT13-3. Plasmids DNAs were prepared using either crude method (alkaline treatment, bacterial DNA precipitation with 3 M KOAc, isopropanol precipitation followed by RNAse treatment and second round of isopropanol precipitation) or plasmid DNA kits from Qiagen Inc. The templates prepared using Qiagen's kits were sequenced.

C. Functional Assay

Transfections were carried out with each clone, using the rat GLP-2R, 587 clone as a positive control for cAMP response to GLP-2 peptide. Methods for transfection, cell culture and cAMP assay were identical to those described for the functional assay of rat, 587 clone. Results showed that although the positive control gave good cAMP response in COS cells, none of the HHT13 clones gave any cAMP response. As confirmed by sequencing which showed a frame-shift mutation, the functional data suggested that no functional GLP-2R protein was expressed from these cDNA clones.

D. Comparison of DNA Sequences Between Rat GLP-2R and HHT13 Subclones

The comparison showed a 2 bp deletion at a position corresponding to nucleotides 389–390 of the rat GLP-2R cDNA, resulting in the loss of nucleotides 374–375 of the human GLP-2R cDNA sequence presented herein.

Insertion of 2 Base Pairs at Position 374 of the Human GLP-2 Receptor cDNA Sequence and Functional Analysis of the Resulting Clone PCR was used to incorporate two bp of the rat GLP-2R DNA sequence into HHT13-1 DNA at the site of the 2 bp frame-shift deletion identified relative to the rat GLP-2R coding sequence. The following primers were designed from HHT13 DNA sequence to insert two bp:

HWBR/2BPI-475F
[5'-ACAGGCATGTCTGGAAGACTTACTCAAGGAACCTTCTGGCAT-3'] (SEQ ID NO: 19)

HWBR/2BPI-506R
[5'-ATGCCAGAAGGTTCCTTGAGTAAGTCTTCCAGACATGCCTGT-3'] (SEQ ID NO: 20)

HWBR-F7 [5'-TTCCTCTGTGGTACCAAGAGGAATGC-3'] (SEQ ID NO: 21)

and

HWBR-1910R:
[5'-GGTGGACTCGAGGTACCGATCTCACTCTCTTCCAGAATC-3'] (SEQ ID NO: 22)

PCR 1: One ng of pHHT13-1 DNA was used as template to do two PCRs with primers, HWBR-F7 vs HWBR/2BPI-506R and HWBR/2BPI-475F vs HWBR-1910R. The Expands™ PCR system from Boehringer Mannheim (Cat. 1681-842) was used under the following conditions:
5 µl of 10× Expand™ Buffer 1
7 µl of 2.5 mM dNTP mix
1.5 µl of primer HWBR-F7 or HWBR/2BPI-475F
1.5 µl of primer HWBR/2BPI-506R or HWBR-1910R
0.75 µl of Expand PCR enzyme (1 unit)
33.25 µl water and
1 µl DNA.

Reaction conditions: 10 cycles of 92° C.—40 sec; 48° C.—1 min; 68° C.—3 min and 30 cycles of 92° C.—40 sec; 55° C.—40 sec; 68° C.—2 min.

The primers HWBR-F7 and HWBR/2BPI-506R amplified a DNA fragment of 400 bp and HWBR/2BPI-475F and HWBR-1910R amplified a DNA fragment of approximately 1.4 kb on an agarose gel. The two bands were cut out of the agarose gel and purified with Qiaquick gel extraction kit from Qiagen Inc. (Cat no. 28706) and the DNAs were eluted in 50 µl of 10 mM Tris (pH 8.5).

PCR 2 (Extension without primers): Approximately 75 ng of two amplified product from above PCR 1 were mixed and then recombined without primers by extending under the following conditions:

2 µl of 10× Expand™ Buffer 1
2.8 µl of 2.5 mM dNTP mix
0.3 µl of Expand PCR enzyme (1 unit)
8.9 µl water
6 µl of combined PCR 1 products Reaction conditions: 15 cycles of 92° C.—1 min; 60° C.—5 min; 68° C.—3 min.

PCR 3: 1 µl of amplified mix from PCR 2 was used as template to amplify with HWBR-F7 and HWBR-1910R primers using the following conditions:
10 µl of 10× Expand™ Buffer 1
14 µl of 2.5 mM dNTP mix
3.0 µl of primer HWBR-F7 or HWBR/2BPI-475F
3.0 µl of primer HWBR/2BPI-506R or HWBR-1910R 1.5 µl of Expand PCR enzyme (1 unit)
67.5 µl water and
1 µl DNA.

Reaction conditions: 30 cycles of 92° C.—1 min; 60° C.—1 min; 68° C.—2 min.

A DNA fragment of approximately 1.7 kb was amplified as seen on an agarose gel. The PCR product was purified using the QIAGEN's QIAquick PCR purification kit (cat. no. 28104) and eluted in 50 µl of 10 mM Tris, pH 8.0. The purified product was restricted with Kpn I and subcloned into Kpn I-restricted pcDNA3.1(-)/Myc-His A (Invitrogen, Cat. no. V855-20). One clone, named pc3.1/HuGL2R/MH6 (pHuMH6), had the 1.7 kb insert in correct orientation as checked by PCR using vector vs. insert primers.

Functional Assay

This hybrid clone was compared to rat GLP-2R using the assay described in Example 2. Results showed that the 2 bp "GA" replacement into the putative deletion site yielded a clone encoding a functional GLP-2R protein, as shown by the cAMP response to GLP-2 treatment.

EXAMPLE 6
Isolation of the Full-Length Human GLP-2 Receptor cDNA

Twenty thousand clones from λgt10 cDNA Library from Human Stomach (Clontech; Cat. HL3017a) were plated on each of 100 agar 150 mm plates. SM buffer (0.1 M NaCl, 10 mM Mg₂So₄, 35 mM Tris, pH-7.5, 0.01% gelatin) was added to each plate to obtain 100 phage lysates each containing 20,000 (20K) pooled clones. The first fifty 20K phage lysates (20K pools) were screened by PCR using two primers designed from HHT13 DNA sequence. The template DNA from each pool was prepared by boiling phage lysate for 10 minutes and centrifuging for 10 minutes.

HWBR-113F [5'-GTGGAGAGGATTTGTGCAAACATTTC-3'] (SEQ ID NO: 23)

HWBR-578R [5'-AGAGACATTTCCAGGAGAAGAATGAG-3'] (SEQ ID NO: 24)

1 µl of each 20K pool DNA was diagnosed by PCR with HWBR-113F and HWBR-578R primers using the following conditions:
2 µl of 10× Expand™ Buffer 1
2.8 µl of 2.5 mM dNTP mix
0.6 µl of primer HWBR-113F
0.6 µl of primer HWBR-578R
0.3 µl of Expand PCR enzyme (1 unit)
12.7 µl water
1 µl 20K pool DNA Reaction conditions: 35 cycles of 92° C.—40 s.; 60° C.—40 s.; 68° C.—1 min.

A DNA fragment of approximately 450 bp was seen in amplification of templates from two pools (HST 19 and HST 38).

B. Screening of Clones from two Positive Pools: HST 19 and HST 38

40,000 clones plated from each of two positive 20K pools were screened by plaque lifts on nitrocellulose filters (Amersham; Cat.RPN137E). The probe was prepared by random primer labeling a DNA fragment from pHHT13-1.

1. The filters were pre-hybridized and hybridized at 42° C. overnight. Hybridization solution consisted of 50% formamide, 5× SSPE, 5× Denhart's solution, 0.5% SDS and salmon sperm DNA (200 mg/ml).
2. After hybridization the filters were washed under the following conditions:
two times at room temperature in 2× SSPE and 0.01% SDS;
two times at 42° C. in 2× SSPE and 0.01% SDS; and
two times at 50° C. in 0.1× SSPE and 0.01% SDS.
3. The filters were autoradiographed and the regions on the plates matching to positive signals were isolated. One positive clone (HST 38-4-30) was isolated from HST 38 pool. 450 bp DNA fragment was amplified from the positive clone by using primers HWBR-113F and HWBR-578R and sequenced. The sequence clearly showed that the plasmid contain 2 bp (AG) at position 373-374 of HHT13 DNA sequence.

The complete insert of clone HST 38-4-30 was amplified using λgt10 primers as described in Example 1. PCR amplified a DNA fragment of approximately 1.4 kb. The amplified DNA was purified and sequenced.

EXAMPLE 4

Reconstruction of a Clone of Full-Length Functional Human GLP-2R cDNA and Functional Assay A 700 bp fragment obtained by Kpn I and Pvu II restriction digest of the amplified DNA from clone HST 38-4-30, and 1.4 kb DNA fragment from Xho I and Pvu II restricted pHHT13-1 DNA were subcloned into Kpn I and Xho I restricted pcDNA3 in a three-way ligation. The new plasmid construct was called pc3/HuGL2R-2. In this manner the full length sequence of the human GLP-2 receptor was obtained.

Functional Assay

The new clone was compared to the rat GLP-2R clone 587 as described previously. Results showed that the clone encoded a functional human GLP-2R protein, which led to cAMP production in COS cells in response to GLP-2 treatment.

EQUIVALENTS

The foregoing written specification is considered to be sufficient to enable one skilled in the art to practice the invention. Indeed, various modifications of the above-described makes for carrying out the invention which are obvious to those skilled in the field of biochemistry, molecular biology or related fields are intended to be within the scope of the following claims.

What is claimed is:

1. An isolated recombinant polynucleotide molecule comprising a nucleic acid encoding the amino acid sequence of SEQ ID NO: 2 or SEQ ID NO: 12, and expression controlling elements linked operably with said nucleic acid to drive expression thereof.

2. The isolated recombinant polynucleotide molecule according to claim 1, adapted for expression in a mammalian cell.

3. The isolated recombinant polynucleotide according to claims 1, wherein the nucleic acid is one having SEQ ID NO: 11.

4. An isolated nucleic acid encoding a GLP-2 receptor, wherein the nucleic acid encodes the amino acid sequence of SEQ ID NO: 12.

5. An isolated nucleic acid encoding a GLP-2 receptor, wherein the nucleic acid encodes the amino acid sequence of SEQ ID NO: 2.

6. The isolated nucleic acid according to claim 5, having SEQ ID NO: 1.

7. A cell that has been genetically engineered by the insertion of nucleic acid coding for the amino acid sequence of SEQ ID NO: 2 or SEQ ID NO: 12.

8. The cell according to claim 7, wherein the nucleic acid is operably linked to expression controlling elements functional in said cell to drive expression of said nucleic acid.

9. The cell according to claim 8, wherein said nucleic acid is one having SEQ ID NO: 1 or SEQ ID NO: 11.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1574 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 17...1543
      (D) OTHER INFORMATION:

(xi) SEQUENCE DESCRIPTION: SEQ ID NO:1:

```
TCTCCACTCC CAACAG ATG CGT CTG CTG TGG GGC CCT GGG AGG CCC TTC CTC      52
               Met Arg Leu Leu Trp Gly Pro Gly Arg Pro Phe Leu
                 1               5                  10

GCC CTG CTT CTG CTG GTT TCC ATC AAG CAA GTT ACA GGA TCG CTC CTC       100
Ala Leu Leu Leu Leu Val Ser Ile Lys Gln Val Thr Gly Ser Leu Leu
         15                  20                  25

AAG GAG ACA ACT CAG AAG TGG GCT AAT TAT AAG GAG AAG TGT CTG GAA       148
Lys Glu Thr Thr Gln Lys Trp Ala Asn Tyr Lys Glu Lys Cys Leu Glu
     30                  35                  40

GAC TTG CAC AAT AGA CTT TCT GGC ATA TTT TGT AAT GGG ACA TTT GAT       196
Asp Leu His Asn Arg Leu Ser Gly Ile Phe Cys Asn Gly Thr Phe Asp
 45                  50                  55                  60

CGG TAT GTG TGC TGG CCT CAT TCT TAT CCT GGA AAT GTC TCT GTT CCC       244
Arg Tyr Val Cys Trp Pro His Ser Tyr Pro Gly Asn Val Ser Val Pro
             65                  70                  75
```

```
TGT CCT TCA TAC TTA CCT TGG TGG AAT GCA GAG AGC CCA GGA AGG GCC       292
Cys Pro Ser Tyr Leu Pro Trp Trp Asn Ala Glu Ser Pro Gly Arg Ala
            80                  85                  90

TAC AGA CAC TGC TTG GCT CAG GGG ACT TGG CAG ACG CGA GAG AAC ACC       340
Tyr Arg His Cys Leu Ala Gln Gly Thr Trp Gln Thr Arg Glu Asn Thr
        95                  100                 105

ACA GAT ATT TGG CAG GAT GAA TCA GAA TGC TCA GAG AAC CAC AGC TTC       388
Thr Asp Ile Trp Gln Asp Glu Ser Glu Cys Ser Glu Asn His Ser Phe
    110                 115                 120

AGA CAA AAC GTG GAT CAC TAC GCC TTG CTA TAC ACC TTG CAG CTG ATG       436
Arg Gln Asn Val Asp His Tyr Ala Leu Leu Tyr Thr Leu Gln Leu Met
125                 130                 135                 140

TAC ACT GTG GGC TAC TCC GTG TCT CTC ATC TCC CTC TTC TTG GCT CTT       484
Tyr Thr Val Gly Tyr Ser Val Ser Leu Ile Ser Leu Phe Leu Ala Leu
                145                 150                 155

ACA CTC TTC TTG TTC CTT CGA AAA CTG CAT TGC ACA CGC AAT TAC ATC       532
Thr Leu Phe Leu Phe Leu Arg Lys Leu His Cys Thr Arg Asn Tyr Ile
            160                 165                 170

CAC ATG AAC CTG TTC GCT TCG TTC ATC CTG AAA GTT CTG GCT GTC CTG       580
His Met Asn Leu Phe Ala Ser Phe Ile Leu Lys Val Leu Ala Val Leu
        175                 180                 185

GTG AAG GAC ATG GTC TCC CAC AAC TCT TAC TCC AAG AGG CCC GAT GAT       628
Val Lys Asp Met Val Ser His Asn Ser Tyr Ser Lys Arg Pro Asp Asp
    190                 195                 200

GAG AGT GGA TGG ATG TCA TAT CTG TCA GAG ACA TCC GTC TCC TGT CGC       676
Glu Ser Gly Trp Met Ser Tyr Leu Ser Glu Thr Ser Val Ser Cys Arg
205                 210                 215                 220

TCC GTC CAG GTC CTC CTG CAC TAC TTT GTG GGC ACC AAT CAC TTG TGG       724
Ser Val Gln Val Leu Leu His Tyr Phe Val Gly Thr Asn His Leu Trp
                225                 230                 235

CTG CTG GTT GAA GGA CTT TAC CTC CAC ACT CTG CTG GAG CCC ACA GTG       772
Leu Leu Val Glu Gly Leu Tyr Leu His Thr Leu Leu Glu Pro Thr Val
            240                 245                 250

TTT CCT GAA AGG CGG CTG TGG CCC AAG TAC CTG GTG GTG GGT TGG GCC       820
Phe Pro Glu Arg Arg Leu Trp Pro Lys Tyr Leu Val Val Gly Trp Ala
        255                 260                 265

TTC CCC ATG CTG TTT GTT ATT CCC TGG GGT TTT GCC CGT GCA CAC CTG       868
Phe Pro Met Leu Phe Val Ile Pro Trp Gly Phe Ala Arg Ala His Leu
    270                 275                 280

GAG AAC ACA CGG TGC TGG GCC ACA AAT GGG AAC CTG AAA ATC TGG TGG       916
Glu Asn Thr Arg Cys Trp Ala Thr Asn Gly Asn Leu Lys Ile Trp Trp
285                 290                 295                 300

ATC ATC AGA GGA CCC ATG CTG CTT TGT GTA ACA GTT AAT TTC TTC ATC       964
Ile Ile Arg Gly Pro Met Leu Leu Cys Val Thr Val Asn Phe Phe Ile
                305                 310                 315

TTC CTC AAG ATT CTC AAG CTT CTC ATT TCT AAG CTC AAA GCT CAT CAG      1012
Phe Leu Lys Ile Leu Lys Leu Leu Ile Ser Lys Leu Lys Ala His Gln
            320                 325                 330

ATG TGC TTC AGA GAC TAC AAA TAC AGA TTG GCG AAA TCA ACG TTG CTC      1060
Met Cys Phe Arg Asp Tyr Lys Tyr Arg Leu Ala Lys Ser Thr Leu Leu
        335                 340                 345

CTC ATT CCT TTG TTG GGG GTT CAT GAG GTC CTC TTC ACT TTC TTC CCC      1108
Leu Ile Pro Leu Leu Gly Val His Glu Val Leu Phe Thr Phe Phe Pro
    350                 355                 360

GAC GAC CAA GTT CAA GGA TTT TCA AAA CGT ATT CGA CTC TTC ATC CAG      1156
Asp Asp Gln Val Gln Gly Phe Ser Lys Arg Ile Arg Leu Phe Ile Gln
365                 370                 375                 380

CTG ACA CTG AGC TCT GTC CAC GGA TTT CTG GTG GCC TTG CAG TAT GGC      1204
Leu Thr Leu Ser Ser Val His Gly Phe Leu Val Ala Leu Gln Tyr Gly
```

-continued

```
                385                 390                 395
TTT GCC AAT GGA GAG GTG AAG GCA GAG CTG CGA AAG TCA TGG GGC CGC       1252
Phe Ala Asn Gly Glu Val Lys Ala Glu Leu Arg Lys Ser Trp Gly Arg
                400                 405                 410

TTC TTA TTA GCC CGC CAC TGG GGC TGC AGA ACC TGT GTC CTG GGG AAG       1300
Phe Leu Leu Ala Arg His Trp Gly Cys Arg Thr Cys Val Leu Gly Lys
                415                 420                 425

AAT TTC CGG TTC CTG GGG AAG TGT TCC AAG AAG CTG TCG GAG GGA GAT       1348
Asn Phe Arg Phe Leu Gly Lys Cys Ser Lys Lys Leu Ser Glu Gly Asp
                430                 435                 440

GGC TCT GAG ACA CTC CAG AAG CTG CGG TTC TCC ACA TGC AGC TCA CAC       1396
Gly Ser Glu Thr Leu Gln Lys Leu Arg Phe Ser Thr Cys Ser Ser His
445                 450                 455                 460

CTG GCC TCT GAG ACC CTG GGA GAC GTT GGG GTA CAG CCT CAC AGG GGC       1444
Leu Ala Ser Glu Thr Leu Gly Asp Val Gly Val Gln Pro His Arg Gly
                465                 470                 475

CGT GGA GCT TGG CCC CGG GGA AGC AGC CTG TCT GAG AGC AGT GAG GGA       1492
Arg Gly Ala Trp Pro Arg Gly Ser Ser Leu Ser Glu Ser Ser Glu Gly
                480                 485                 490

GAC TTC ACC CTG GCC AAT ACG ATG GAG GAG ATT CTG GAA GAG AGT GAG       1540
Asp Phe Thr Leu Ala Asn Thr Met Glu Glu Ile Leu Glu Glu Ser Glu
                495                 500                 505

ATC TAAGGCAGGG TCCATCACCG CAGCTTGGCC A                                1574
Ile
```

(2) INFORMATION FOR SEQ ID NO:2:

(i) SEQUENCE CHARACTERISTICS:
        (A) LENGTH: 509 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

```
Met Arg Leu Leu Trp Gly Pro Gly Arg Pro Phe Leu Ala Leu Leu Leu
1               5                   10                  15

Leu Val Ser Ile Lys Gln Val Thr Gly Ser Leu Leu Lys Glu Thr Thr
                20                  25                  30

Gln Lys Trp Ala Asn Tyr Lys Glu Lys Cys Leu Glu Asp Leu His Asn
                35                  40                  45

Arg Leu Ser Gly Ile Phe Cys Asn Gly Thr Phe Asp Arg Tyr Val Cys
            50                  55                  60

Trp Pro His Ser Tyr Pro Gly Asn Val Ser Val Pro Cys Pro Ser Tyr
65              70                  75                  80

Leu Pro Trp Trp Asn Ala Glu Ser Pro Gly Arg Ala Tyr Arg His Cys
                85                  90                  95

Leu Ala Gln Gly Thr Trp Gln Thr Arg Glu Asn Thr Thr Asp Ile Trp
                100                 105                 110

Gln Asp Glu Ser Glu Cys Ser Glu Asn His Ser Phe Arg Gln Asn Val
                115                 120                 125

Asp His Tyr Ala Leu Leu Tyr Thr Leu Gln Leu Met Tyr Thr Val Gly
            130                 135                 140

Tyr Ser Val Ser Leu Ile Ser Leu Phe Leu Ala Leu Thr Leu Phe Leu
145                 150                 155                 160

Phe Leu Arg Lys Leu His Cys Thr Arg Asn Tyr Ile His Met Asn Leu
                165                 170                 175
```

-continued

```
Phe Ala Ser Phe Ile Leu Lys Val Leu Ala Val Leu Val Lys Asp Met
            180                 185                 190

Val Ser His Asn Ser Tyr Ser Lys Arg Pro Asp Asp Glu Ser Gly Trp
            195                 200                 205

Met Ser Tyr Leu Ser Glu Thr Ser Val Ser Cys Arg Ser Val Gln Val
            210                 215                 220

Leu Leu His Tyr Phe Val Gly Thr Asn His Leu Trp Leu Leu Val Glu
225                 230                 235                 240

Gly Leu Tyr Leu His Thr Leu Leu Glu Pro Thr Val Phe Pro Glu Arg
            245                 250                 255

Arg Leu Trp Pro Lys Tyr Leu Val Val Gly Trp Ala Phe Pro Met Leu
            260                 265                 270

Phe Val Ile Pro Trp Gly Phe Ala Arg Ala His Leu Glu Asn Thr Arg
            275                 280                 285

Cys Trp Ala Thr Asn Gly Asn Leu Lys Ile Trp Trp Ile Ile Arg Gly
            290                 295                 300

Pro Met Leu Leu Cys Val Thr Val Asn Phe Phe Ile Phe Leu Lys Ile
305                 310                 315                 320

Leu Lys Leu Leu Ile Ser Lys Leu Lys Ala His Gln Met Cys Phe Arg
            325                 330                 335

Asp Tyr Lys Tyr Arg Leu Ala Lys Ser Thr Leu Leu Leu Ile Pro Leu
            340                 345                 350

Leu Gly Val His Glu Val Leu Phe Thr Phe Phe Pro Asp Asp Gln Val
            355                 360                 365

Gln Gly Phe Ser Lys Arg Ile Arg Leu Phe Ile Gln Leu Thr Leu Ser
            370                 375                 380

Ser Val His Gly Phe Leu Val Ala Leu Gln Tyr Gly Phe Ala Asn Gly
385                 390                 395                 400

Glu Val Lys Ala Glu Leu Arg Lys Ser Trp Gly Arg Phe Leu Leu Ala
            405                 410                 415

Arg His Trp Gly Cys Arg Thr Cys Val Leu Gly Lys Asn Phe Arg Phe
            420                 425                 430

Leu Gly Lys Cys Ser Lys Lys Leu Ser Glu Gly Asp Gly Ser Glu Thr
            435                 440                 445

Leu Gln Lys Leu Arg Phe Ser Thr Cys Ser Ser His Leu Ala Ser Glu
            450                 455                 460

Thr Leu Gly Asp Val Gly Val Gln Pro His Arg Gly Arg Gly Ala Trp
465                 470                 475                 480

Pro Arg Gly Ser Ser Leu Ser Glu Ser Glu Gly Asp Phe Thr Leu
            485                 490                 495

Ala Asn Thr Met Glu Glu Ile Leu Glu Glu Ser Glu Ile
            500                 505
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TTTTTCTAGA ASRTSATSTA CACNGTSGGC TAC                       33

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTTTCTCGAG CCARCARCCA SSWRTARTTG GC                                    32

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AACTACATCC ACMKGMAYCT GTTYVYGTCB TTCATSCT                            38

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCATCTCCCT CTTCTTGGCT CTTAC                                                25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TCTGACAGAT ATGACATCCA TCCAC                                                25

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TCYRNCTGSA CCTCMYYRTT GASRAARCAG TA                                    32

(2) INFORMATION FOR SEQ ID NO:9:

(i) SEQUENCE CHARACTERISTICS:
        (A) LENGTH: 667 base pairs

```
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: Coding Sequence
            (B) LOCATION: 1...666
            (D) OTHER INFORMATION:

(xi) SEQUENCE DESCRIPTION: SEQ ID NO:9:

TCC TTC TCT CTT ATC TCC CTC TTC CTG GCT CTC ACC CTC CTC TTG TTT       48
Ser Phe Ser Leu Ile Ser Leu Phe Leu Ala Leu Thr Leu Leu Leu Phe
 1               5                  10                  15

CTT CGA AAA CTC CAC TGC ACG CGC AAC TAC ATC CAC ATG AAC TTG TTT       96
Leu Arg Lys Leu His Cys Thr Arg Asn Tyr Ile His Met Asn Leu Phe
             20                  25                  30

GCT TCT TTC ATC CTG AGA ACC CTG GCT GTA CTG GTG AAG GAC GTC GTC      144
Ala Ser Phe Ile Leu Arg Thr Leu Ala Val Leu Val Lys Asp Val Val
         35                  40                  45

TTC TAC AAC TCT TAC TCC AAG AGG CCT GAC AAT GAG AAT GGG TGG ATG      192
Phe Tyr Asn Ser Tyr Ser Lys Arg Pro Asp Asn Glu Asn Gly Trp Met
     50                  55                  60

TCC TAC CTG TCA GAG ATG TCC ACC TCC TGC CGC TCA GTC CAG GTT CTC      240
Ser Tyr Leu Ser Glu Met Ser Thr Ser Cys Arg Ser Val Gln Val Leu
 65                  70                  75                  80

TTG CAT TAC TTT GTG GGT GCC AAT TAC TTA TGG CTG CTG GTT GAA GGC      288
Leu His Tyr Phe Val Gly Ala Asn Tyr Leu Trp Leu Leu Val Glu Gly
                 85                  90                  95

CTC TAC CTC CAC ACG CTG CTG GAG CCC ACA GTG CTT CCT GAG AGG CGG      336
Leu Tyr Leu His Thr Leu Leu Glu Pro Thr Val Leu Pro Glu Arg Arg
            100                 105                 110

CTG TGG CCC AGA TAC CTG CTG TTG GGT TGG GCC TTC CCT GTG CTA TTT      384
Leu Trp Pro Arg Tyr Leu Leu Leu Gly Trp Ala Phe Pro Val Leu Phe
        115                 120                 125

GTT GTA CCC TGG GGT TTC GCC CGT GCA CAC CTG GAG AAC ACA GGG TGC      432
Val Val Pro Trp Gly Phe Ala Arg Ala His Leu Glu Asn Thr Gly Cys
    130                 135                 140

TGG ACA ACA AAT GGG AAT AAG AAA ATC TGG TGG ATC ATC CGA GGA CCC      480
Trp Thr Thr Asn Gly Asn Lys Lys Ile Trp Trp Ile Ile Arg Gly Pro
145                 150                 155                 160

ATG ATG CTC TGT GTA ACA GTC AAT TTC TTC ATC TTC CTG AAA ATT CTC      528
Met Met Leu Cys Val Thr Val Asn Phe Phe Ile Phe Leu Lys Ile Leu
                165                 170                 175

AAG CTT CTC ATT TCT AAG CTC AAA GCT CAT CAA ATG TGC TTC AGA GAT      576
Lys Leu Leu Ile Ser Lys Leu Lys Ala His Gln Met Cys Phe Arg Asp
            180                 185                 190

TAT AAA TAC AGA TTG GCA AAA TCA ACA CTG GTC CTC ATT CCT TTA TTG      624
Tyr Lys Tyr Arg Leu Ala Lys Ser Thr Leu Val Leu Ile Pro Leu Leu
        195                 200                 205

GGC GTT CAT GAG ATC CTC TTC TCT TTC ATC ACT GAT GAT CAA G            667
Gly Val His Glu Ile Leu Phe Ser Phe Ile Thr Asp Asp Gln
    210                 215                 220

(2) INFORMATION FOR SEQ ID NO:10:

(i) SEQUENCE CHARACTERISTICS:
            (A) LENGTH: 222 amino acids
            (B) TYPE: amino acid
            (C) STRANDEDNESS:
            (D) TOPOLOGY: unknown (ii) MOLECULE TYPE: protein
```

(xi) SEQUENCE DESCRIPTION: SEQ ID NO:10:

```
Ser Phe Ser Leu Ile Ser Leu Phe Leu Ala Leu Thr Leu Leu Leu Phe
 1               5                  10                  15

Leu Arg Lys Leu His Cys Thr Arg Asn Tyr Ile His Met Asn Leu Phe
            20                  25                  30

Ala Ser Phe Ile Leu Arg Thr Leu Ala Val Leu Val Lys Asp Val Val
        35                  40                  45

Phe Tyr Asn Ser Tyr Ser Lys Arg Pro Asp Asn Glu Asn Gly Trp Met
 50                  55                  60

Ser Tyr Leu Ser Glu Met Ser Thr Ser Cys Arg Ser Val Gln Val Leu
65                  70                  75                  80

Leu His Tyr Phe Val Gly Ala Asn Tyr Leu Trp Leu Val Glu Gly
                85                  90                  95

Leu Tyr Leu His Thr Leu Leu Glu Pro Thr Val Leu Pro Glu Arg Arg
            100                 105                 110

Leu Trp Pro Arg Tyr Leu Leu Leu Gly Trp Ala Phe Pro Val Leu Phe
            115                 120                 125

Val Val Pro Trp Gly Phe Ala Arg Ala His Leu Glu Asn Thr Gly Cys
130                 135                 140

Trp Thr Thr Asn Gly Asn Lys Lys Ile Trp Trp Ile Ile Arg Gly Pro
145                 150                 155                 160

Met Met Leu Cys Val Thr Val Asn Phe Phe Ile Phe Leu Lys Ile Leu
                165                 170                 175

Lys Leu Leu Ile Ser Lys Leu Lys Ala His Gln Met Cys Phe Arg Asp
            180                 185                 190

Tyr Lys Tyr Arg Leu Ala Lys Ser Thr Leu Val Leu Ile Pro Leu Leu
            195                 200                 205

Gly Val His Glu Ile Leu Phe Ser Phe Ile Thr Asp Asp Gln
210                 215                 220
```

(2) INFORMATION FOR SEQ ID NO:11:

(i) SEQUENCE CHARACTERISTICS:
        (A) LENGTH: 2112 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 122...1780
        (D) OTHER INFORMATION:

(xi) SEQUENCE DESCRIPTION: SEQ ID NO:11:

```
TGGAGAGGAT TTGTGCAAAC ATTTCTTCTG TGGACCAAGA GGAATGCAAG AGGAGGCTGC      60

CTGCGGTGCA TCTTGGACGG CTAGAGAGAT GTACCCCTAC TTGTGAAGGT GCACGAGGAA     120

G ATG AAG CTG GGA TCG AGC AGG GCA GGG CCT GGG AGA GGA AGC GCG GGA     169
  Met Lys Leu Gly Ser Ser Arg Ala Gly Pro Gly Arg Gly Ser Ala Gly
   1               5                  10                  15

CTC CTG CCT GGC GTC CAC GAG CTG CCC ATG GGC ATC CCT GCC CCC TGG      217
Leu Leu Pro Gly Val His Glu Leu Pro Met Gly Ile Pro Ala Pro Trp
             20                  25                  30

GGG ACC AGT CCT CTC TCC TTC CAC AGG AAG TGC TCT CTC TGG GCC CCT      265
Gly Thr Ser Pro Leu Ser Phe His Arg Lys Cys Ser Leu Trp Ala Pro
         35                  40                  45
```

-continued

| | | |
|---|---|---|
| GGG AGG CCC TTC CTC ACT CTG GTC CTG CTG GTT TCC ATC AAG CAA GTT<br>Gly Arg Pro Phe Leu Thr Leu Val Leu Leu Val Ser Ile Lys Gln Val<br>50              55                  60 | 313 |
| ACA GGA TCC CTC CTT GAG GAA ACG ACT CGG AAG TGG GCT CAG TAC AAA<br>Thr Gly Ser Leu Leu Glu Glu Thr Thr Arg Lys Trp Ala Gln Tyr Lys<br>65              70                  75                  80 | 361 |
| CAG GCA TGT CTG AGA GAC TTA CTC AAG GAA CCT TCT GGC ATA TTT TGT<br>Gln Ala Cys Leu Arg Asp Leu Leu Lys Glu Pro Ser Gly Ile Phe Cys<br>                85                  90                  95 | 409 |
| AAC GGG ACA TTT GAT CAG TAC GTG TGT TGG CCT CAT TCT TCT CCT GGA<br>Asn Gly Thr Phe Asp Gln Tyr Val Cys Trp Pro His Ser Ser Pro Gly<br>                100                 105                 110 | 457 |
| AAT GTC TCT GTA CCC TGC CCT TCA TAC TTA CCT TGG TGG AGT GAA GAG<br>Asn Val Ser Val Pro Cys Pro Ser Tyr Leu Pro Trp Trp Ser Glu Glu<br>                115                 120                 125 | 505 |
| AGC TCA GGA AGG GCC TAC AGA CAC TGC TTG GCT CAG GGG ACT TGG CAG<br>Ser Ser Gly Arg Ala Tyr Arg His Cys Leu Ala Gln Gly Thr Trp Gln<br>130                 135                 140 | 553 |
| ACG ATA GAG AAC GCC ACG GAT ATT TGG CAG GAT GAC TCC GAA TGC TCC<br>Thr Ile Glu Asn Ala Thr Asp Ile Trp Gln Asp Asp Ser Glu Cys Ser<br>145                 150                 155                 160 | 601 |
| GAG AAC CAC AGC TTC AAG CAA AAC GTG GAC CGT TAT GCC TTG CTG TCA<br>Glu Asn His Ser Phe Lys Gln Asn Val Asp Arg Tyr Ala Leu Leu Ser<br>                165                 170                 175 | 649 |
| ACC TTG CAG CTG ATG TAC ACC GTG GGA TAC TCC TTC TCT CTT ATC TCC<br>Thr Leu Gln Leu Met Tyr Thr Val Gly Tyr Ser Phe Ser Leu Ile Ser<br>                180                 185                 190 | 697 |
| CTC TTC CTG GCT CTC ACC CTC CTC TTG TTT CTT CGA AAA CTC CAC TGC<br>Leu Phe Leu Ala Leu Thr Leu Leu Leu Phe Leu Arg Lys Leu His Cys<br>                195                 200                 205 | 745 |
| ACG CGC AAC TAC ATC CAC ATG AAC TTG TTT GCT TCT TTC ATC CTG AGA<br>Thr Arg Asn Tyr Ile His Met Asn Leu Phe Ala Ser Phe Ile Leu Arg<br>210                 215                 220 | 793 |
| ACC CTG GCT GTA CTG GTG AAG GAC GTC GTC TTC TAC AAC TCT TAC TCC<br>Thr Leu Ala Val Leu Val Lys Asp Val Val Phe Tyr Asn Ser Tyr Ser<br>225                 230                 235                 240 | 841 |
| AAG AGG CCT GAC AAT GAG AAT GGG TGG ATG TCC TAC CTG TCA GAG ATG<br>Lys Arg Pro Asp Asn Glu Asn Gly Trp Met Ser Tyr Leu Ser Glu Met<br>                245                 250                 255 | 889 |
| TCC ACC TCC TGC CGC TCA GTC CAG GTT CTC TTG CAT TAC TTT GTG GGT<br>Ser Thr Ser Cys Arg Ser Val Gln Val Leu Leu His Tyr Phe Val Gly<br>                260                 265                 270 | 937 |
| GCC AAT TAC TTA TGG CTG CTG GTT GAA GGC CTC TAC CTC CAC ACG CTG<br>Ala Asn Tyr Leu Trp Leu Leu Val Glu Gly Leu Tyr Leu His Thr Leu<br>                275                 280                 285 | 985 |
| CTG GAG CCC ACA GTG CTT CCT GAG AGG CGG CTG TGG CCC AGA TAC CTG<br>Leu Glu Pro Thr Val Leu Pro Glu Arg Arg Leu Trp Pro Arg Tyr Leu<br>290                 295                 300 | 1033 |
| CTG TTG GGT TGG GCC TTC CCT GTG CTA TTT GTT GTA CCC TGG GGT TTC<br>Leu Leu Gly Trp Ala Phe Pro Val Leu Phe Val Val Pro Trp Gly Phe<br>305                 310                 315                 320 | 1081 |
| GCC CGT GCA CAC CTG GAG AAC ACA GGG TGC TGG ACA ACA AAT GGG AAT<br>Ala Arg Ala His Leu Glu Asn Thr Gly Cys Trp Thr Thr Asn Gly Asn<br>                325                 330                 335 | 1129 |
| AAG AAA ATC TGG TGG ATC ATC CGA GGA CCC ATG ATG CTC TGT GTA ACA<br>Lys Lys Ile Trp Trp Ile Ile Arg Gly Pro Met Met Leu Cys Val Thr<br>                340                 345                 350 | 1177 |
| GTC AAT TTC TTC ATC TTC CTG AAA ATT CTC AAG CTT CTC ATT TCT AAG<br>Val Asn Phe Phe Ile Phe Leu Lys Ile Leu Lys Leu Leu Ile Ser Lys<br>                355                 360                 365 | 1225 |

```
CTC AAA GCT CAT CAA ATG TGC TTC AGA GAT TAT AAA TAC AGA TTG GCA    1273
Leu Lys Ala His Gln Met Cys Phe Arg Asp Tyr Lys Tyr Arg Leu Ala
        370                 375                 380

AAA TCA ACA CTG GTC CTC ATT CCT TTA TTG GGC GTT CAT GAG ATC CTC    1321
Lys Ser Thr Leu Val Leu Ile Pro Leu Leu Gly Val His Glu Ile Leu
385                 390                 395                 400

TTC TCT TTC ATC ACT GAT GAT CAA GTT GAA GGA TTT GCA AAA CTT ATA    1369
Phe Ser Phe Ile Thr Asp Asp Gln Val Glu Gly Phe Ala Lys Leu Ile
                405                 410                 415

CGA CTT TTC ATT CAG TTG ACA CTG AGC TCC TTT CAT GGG TTC CTG GTG    1417
Arg Leu Phe Ile Gln Leu Thr Leu Ser Ser Phe His Gly Phe Leu Val
            420                 425                 430

GCC TTG CAG TAT GGT TTT GCC AAT GGA GAA GTG AAG GCT GAG CTG CGG    1465
Ala Leu Gln Tyr Gly Phe Ala Asn Gly Glu Val Lys Ala Glu Leu Arg
                435                 440                 445

AAA TAC TGG GTC CGC TTC TTG CTA GCC CGC CAC TCA GGC TGC AGA GCC    1513
Lys Tyr Trp Val Arg Phe Leu Leu Ala Arg His Ser Gly Cys Arg Ala
450                 455                 460

TGT GTC CTG GGG AAG GAC TTC CGG TTC CTA GGA AAA TGT CCC AAG AAG    1561
Cys Val Leu Gly Lys Asp Phe Arg Phe Leu Gly Lys Cys Pro Lys Lys
465                 470                 475                 480

CTC TCG GAA GGA GAT GGC GCT GAG AAG CTT CGG AAG CTG CAG CCC TCA    1609
Leu Ser Glu Gly Asp Gly Ala Glu Lys Leu Arg Lys Leu Gln Pro Ser
                485                 490                 495

CTT AAC AGT GGG CGG CTC CTA CAT CTA GCC ATG CGA GGT CTT GGG GAG    1657
Leu Asn Ser Gly Arg Leu Leu His Leu Ala Met Arg Gly Leu Gly Glu
            500                 505                 510

CTG GGC GCC CAG CCC CAA CAG GAC CAT GCA CGC TGG CCC CGG GGC AGC    1705
Leu Gly Ala Gln Pro Gln Gln Asp His Ala Arg Trp Pro Arg Gly Ser
                515                 520                 525

AGC CTG TCC GAG TGC AGT GAG GGG GAT GTC ACC ATG GCC AAC ACC ATG    1753
Ser Leu Ser Glu Cys Ser Glu Gly Asp Val Thr Met Ala Asn Thr Met
            530                 535                 540

GAG GAG ATT CTG GAA GAG AGT GAG ATC TAGGGTGGAG TTCCACCACC CTGGCTC  1807
Glu Glu Ile Leu Glu Glu Ser Glu Ile
545                 550

TGCTCCCAGG GACTCTTGAG GGGGCCCAGG AAGAGGAAGC AAAGCAGGAC ACACGTTGCT  1867

GGGCACGGAA TCATTCTCGT TCCATTCACC ATGCCACTTT GATATGAAAG CTATCACAAG  1927

GTTCTTCAAG CTCTGTATGA AAGAGGCTGT GTGTCATGCT CACAGCCTCT GCCTGCTCTT  1987

CTCATCCTAA TAACCCCCAC CAGTGTGTTT TCCACAATGC CCACCAGACC CTAGGGCCTG  2047

GCTCTAAATT CAAGCCAATG AAGTCCCACC CGGAATTCTT TTGCTTTTTA CCCCTGGAAG  2107

AAATA                                                              2112

(2) INFORMATION FOR SEQ ID NO:12:

(i) SEQUENCE CHARACTERISTICS:
        (A) LENGTH: 553 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:12:

Met Lys Leu Gly Ser Ser Arg Ala Gly Pro Gly Arg Gly Ser Ala Gly
1               5                   10                  15

Leu Leu Pro Gly Val His Glu Leu Pro Met Gly Ile Pro Ala Pro Trp
            20                  25                  30
```

```
Gly Thr Ser Pro Leu Ser Phe His Arg Lys Cys Ser Leu Trp Ala Pro
         35                  40                  45

Gly Arg Pro Phe Leu Thr Leu Val Leu Leu Val Ser Ile Lys Gln Val
     50                  55                  60

Thr Gly Ser Leu Leu Glu Glu Thr Thr Arg Lys Trp Ala Gln Tyr Lys
 65                  70                  75                  80

Gln Ala Cys Leu Arg Asp Leu Leu Lys Glu Pro Ser Gly Ile Phe Cys
                 85                  90                  95

Asn Gly Thr Phe Asp Gln Tyr Val Cys Trp Pro His Ser Ser Pro Gly
             100                 105                 110

Asn Val Ser Val Pro Cys Pro Ser Tyr Leu Pro Trp Trp Ser Glu Glu
             115                 120                 125

Ser Ser Gly Arg Ala Tyr Arg His Cys Leu Ala Gln Gly Thr Trp Gln
         130                 135                 140

Thr Ile Glu Asn Ala Thr Asp Ile Trp Gln Asp Ser Glu Cys Ser
145                 150                 155                 160

Glu Asn His Ser Phe Lys Gln Asn Val Asp Arg Tyr Ala Leu Leu Ser
                 165                 170                 175

Thr Leu Gln Leu Met Tyr Thr Val Gly Tyr Ser Phe Ser Leu Ile Ser
             180                 185                 190

Leu Phe Leu Ala Leu Thr Leu Leu Phe Leu Arg Lys Leu His Cys
         195                 200                 205

Thr Arg Asn Tyr Ile His Met Asn Leu Phe Ala Ser Phe Ile Leu Arg
         210                 215                 220

Thr Leu Ala Val Leu Val Lys Asp Val Val Phe Tyr Asn Ser Tyr Ser
225                 230                 235                 240

Lys Arg Pro Asp Asn Glu Asn Gly Trp Met Ser Tyr Leu Ser Glu Met
             245                 250                 255

Ser Thr Ser Cys Arg Ser Val Gln Val Leu Leu His Tyr Phe Val Gly
                 260                 265                 270

Ala Asn Tyr Leu Trp Leu Leu Val Glu Gly Leu Tyr Leu His Thr Leu
             275                 280                 285

Leu Glu Pro Thr Val Leu Pro Glu Arg Arg Leu Trp Pro Arg Tyr Leu
     290                 295                 300

Leu Leu Gly Trp Ala Phe Pro Val Leu Phe Val Val Pro Trp Gly Phe
305                 310                 315                 320

Ala Arg Ala His Leu Glu Asn Thr Gly Cys Trp Thr Thr Asn Gly Asn
             325                 330                 335

Lys Lys Ile Trp Trp Ile Ile Arg Gly Pro Met Met Leu Cys Val Thr
             340                 345                 350

Val Asn Phe Phe Ile Phe Leu Lys Ile Leu Lys Leu Leu Ile Ser Lys
             355                 360                 365

Leu Lys Ala His Gln Met Cys Phe Arg Asp Tyr Lys Tyr Arg Leu Ala
     370                 375                 380

Lys Ser Thr Leu Val Leu Ile Pro Leu Leu Gly Val His Glu Ile Leu
385                 390                 395                 400

Phe Ser Phe Ile Thr Asp Asp Gln Val Glu Gly Phe Ala Lys Leu Ile
                 405                 410                 415

Arg Leu Phe Ile Gln Leu Thr Leu Ser Ser Phe His Gly Phe Leu Val
             420                 425                 430

Ala Leu Gln Tyr Gly Phe Ala Asn Gly Glu Val Lys Ala Glu Leu Arg
         435                 440                 445
```

```
Lys Tyr Trp Val Arg Phe Leu Leu Ala Arg His Ser Gly Cys Arg Ala
    450                 455                 460
Cys Val Leu Gly Lys Asp Phe Arg Phe Leu Gly Lys Cys Pro Lys Lys
465                 470                 475                 480
Leu Ser Glu Gly Asp Gly Ala Glu Lys Leu Arg Lys Leu Gln Pro Ser
                    485                 490                 495
Leu Asn Ser Gly Arg Leu Leu His Leu Ala Met Arg Gly Leu Gly Glu
                500                 505                 510
Leu Gly Ala Gln Pro Gln Gln Asp His Ala Arg Trp Pro Arg Gly Ser
                515                 520                 525
Ser Leu Ser Glu Cys Ser Glu Gly Asp Val Thr Met Ala Asn Thr Met
            530                 535                 540
Glu Glu Ile Leu Glu Glu Ser Glu Ile
545                 550
```

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AACCCACTGC TTAC                                               14

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CCCAGAATAG AATGACACC                                   19

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CAGGGGCCGG TACCTCTCCA CTCC                             24

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
TTGGGTCCTC GAGTGGCCAA GCTGCG                                              26

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGGTAGTCGG TACCTCTAGA GCAAGTTCAG CC                                       32

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

ATAACAGAGG ATCCTCGAGT ATTTCTTCCA G                                        31

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ACAGGCATGT CTGGAAGACT TACTCAAGGA ACCTTCTGGC AT                            42

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ATGCCAGAAG GTTCCTTGAG TAAGTCTTCC AGACATGCCT GT                            42

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTCCTCTGTG GTACCAAGAG GAATGC                                              26

(2) INFORMATION FOR SEQ ID NO:22:
```

```
        (i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:22:

GGTGGACTCG AGGTACCGAT CTCACTCTCT TCCAGAATC                                    39

(2) INFORMATION FOR SEQ ID NO:23:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:23:

GTGGAGAGGA TTTGTGCAAA CATTTC                                                  26

(2) INFORMATION FOR SEQ ID NO:24:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:24:

AGAGACATTT CCAGGAGAAG AATGAG                                                  26
```